US007910314B2

(12) United States Patent
Frackelton, Jr. et al.

(10) Patent No.: US 7,910,314 B2
(45) Date of Patent: Mar. 22, 2011

(54) SHC PROTEIN-RELATED METHODS AND COMPOSITIONS FOR THE PROGNOSIS OF BREAST, PROSTATE AND OVARIAN CANCER

(75) Inventors: A. Raymond Frackelton, Jr., Rumford, RI (US); Pamela A. Davol, Swansea, MA (US)

(73) Assignee: Roger Williams Hospital, Providence, RI (US)

( * ) Notice: Subject to any disclaimer, the term of this patent is extended or adjusted under 35 U.S.C. 154(b) by 940 days.

(21) Appl. No.: 10/376,538

(22) Filed: Feb. 28, 2003

(65) Prior Publication Data

US 2004/0033542 A1    Feb. 19, 2004

Related U.S. Application Data

(60) Provisional application No. 60/360,758, filed on Mar. 1, 2002.

(51) Int. Cl.
    *G01N 33/53*    (2006.01)
    *C12Q 1/68*     (2006.01)
(52) U.S. Cl. ............................................. 435/7.1; 435/6
(58) Field of Classification Search .................. None
    See application file for complete search history.

(56) References Cited

U.S. PATENT DOCUMENTS

| 5,912,183 | A | 6/1999 | Comoglio et al. |
| 6,025,145 | A | 2/2000 | Godowski et al. |
| 6,492,138 | B1 | 12/2002 | McGlade et al. |
| 6,673,914 | B1 * | 1/2004 | Hoon ........................... 536/23.5 |
| 6,777,415 | B2 | 8/2004 | Daley et al. |
| 7,572,886 | B2 | 8/2009 | Girard et al. |
| 2004/0209809 | A1 | 10/2004 | Saucier et al. |
| 2005/0004008 | A1 | 1/2005 | Frackelton et al. |
| 2007/0060539 | A1 | 3/2007 | Frackelton, Jr. et al. |
| 2008/0132462 | A1 | 6/2008 | Frackelton, Jr. et al. |
| 2008/0299590 | A1 | 12/2008 | Frackelton, Jr. et al. |
| 2009/0220965 | A1 | 9/2009 | Frackelton, Jr. et al. |

FOREIGN PATENT DOCUMENTS

| JP | 2002-539789 | 11/2002 |
| WO | WO 00/56886 | 11/2002 |
| WO | WO 03/073821 | 9/2003 |
| WO | WO 2005/038005 A2 | 4/2005 |
| WO | WO 2007/058965 A1 | 5/2007 |

OTHER PUBLICATIONS

Jackson JG et al. Clinical Cancer Research 6:1135-1139, 2000.*
Xie Y. et al. Biochemical and Biophysical Research Communications 221: 140-145, 1996.*
Comb MJ. The NEB Transcript 7(1): 1-4, Dec. 1995.*
Mathew, A., Pandey, M., and Murthy, N.S. Survival analysis: caveats and pitfalls. 1999. European Journal of Surgical Oncology. vol. 25, pp. 321-329.*
Ohno-Machado, L. Modeling medical prognosis: survival analysis techniques. 2001. Journal of Biomedical Informatics. vol. 34, pp. 428-439.*
Definition of Stroma. American Association for Cancer Research, Glossary of Cancer Terms, 2006.*
Harvey, J.M., Clark, G.M., Osborne, C.K., and Allred, D.C. Estrogen receptor status by immunohistochemistry is superior to the ligand-binding assay for predicting response to adjuvant endocrine therapy in breast cancer. Journal of Clinical Oncology, 1999. vol. 17, pp. 1474-1481.*
Ronnov-Jessen, L., Peterson, O.W., and Bissell, M.J. Cellular changes involved in conversion of normal to malignant breast: importance of the stromal reaction. Physiological Reviews, 1996. vol. 76, pp. 69-125.*
Van'T Veer, L.J., Dai, H., Van De Vijver, M.J., He, Y.D., Hart, A.A.M, Mao, M., Peterse, H.L., Van Der Kooy, K., Marton, M.J., Witteveen, A.T., Schreiber, G.J., Kerkhoven, R.M., Roberts, C., Linsley, P.S., Bernards, R., and Friend, S.H. Gene expression profiling predicts clinical outcome of breast cancer. Nature, 2002. vol. 415, pp. 530-536.*
Lee, Igawa, Chen, Bemmel, Lin, Lin, Johansson, Christman, and Lin. p66-Shc protein is upregulated by steroid hormones in hormone-sensitive cancer cells and in primary prostate carcinomas. International Journal of Cancer, 2004. vol. 108, pp. 672-678.*
Veeramani, Igawa, Yuan, Lin, Lee, Lin, Johansson, and Lin. Expression of p66-Shc protein correlates with proliferation of human prostate cancer cells. Oncogene, 2005. vol. 24, pp. 7203-7212.*
Xie and Hung. p66 isoform down-regulated and not required for HER-2/neu signaling pathway in human breast cancer cell lines with HER-2/neu overexpression. Biochemical and Biophysical Research Communications, 1996. vol. 221, pp. 140-145.*
Gura T., "Systems for Identifying New Drugs are Often Faulty," *Science* 278: 1041-1042 (1997).
Jain, R.K., "Barriers to Drug Delivery in Solid Tumors," *Scientific American*, pp. 58-65, (1994).
Kisielow, M. et al., "Isoform-Specific Knockdown and Expression of Adaptor Protein ShcA Using Small Interfering Rna," *Biochem J.* 363:1-5 (2002).
Le, S., et al., "c-Jun N-terminal Kinase Specifically Phosphorylates p66ShcA at Serine 36 in Response to Ultraviolet Irradiation," *J. Biol. Chem.* 276(51):48332-48336 (2001). MSNBC News Services, "Mixed Results on a New Cancer Drug," pp. 1-4 Nov. 9, 2000.
Murayama, Y., "Growth-inhibitory Effects of Epidermal Growth Factor on Human Breast Cancer and Carcinoma of the Esophagus Transplanted Into Nude Mice, "*Ann. Surg.* 211(3):263-268 (1990).
Sato, K., et al., "Adaptor Protein Shc is an Isoform-Specific Direct Activator of the Tyrosine Kinase c-Src," *J Biol. Chem.*, 277(33):29568-29576 (2002).

(Continued)

*Primary Examiner* — Anne M. Gussow
(74) *Attorney, Agent, or Firm* — Hamilton, Brook, Smith & Reynolds, P.C.

(57) ABSTRACT

This invention provides methods for determining whether a breast, prostate or ovarian tumor or tumor cell is aggressive, based on the quantitative measurement of p66-Shc and phosphorylated Shc. This invention also provides related methods of determining the likelihood of tumor recurrence. This invention further provides a method for determining whether a tumor can be successfully treated using a tyrosine kinase inhibitor. Finally, this invention provides antibodies and kits for practicing the instant methods.

27 Claims, 13 Drawing Sheets

OTHER PUBLICATIONS

U.S. Appl. No. 10/687,396, filed Oct. 15, 2003, Frackelton, et al. (Exhibit 1).

American Cancer Society, "Breast cancer facts & figures 2001-2002." *American Cancer Society Surveillance Research.* (2001) (Exhibit 2).

Andrechek, E.R., et al., "Tyrosine kinase signaling in breast cancer: tyrosine kinase-mediated signal transduction in transgenic mouse models of human breast cancer." *Breast Cancer Res.*, 2(3):211-6. (2000)(Exhibit 3).

Batzer, A.G., et al., "Hierarchy of binding sites for Grb2 and Shc on the epidermal growth factor receptor." *Mol. Cell. Biol.*, 14(8):5192-201. (1994) (Exhibit 4).

Baumann, C. A., et al., "CAP defines a second signaling pathway required for insulin-stimulated glucose transport." *Nature*, 407(6801):202-7. (2000) (Exhibit 5).

Ben-Levy, R., et al., "A single autophosphorylation site confers oncogenicity to the Neu/ErbB-2 receptor and enables coupling to the MAP kinase pathway." *EMBO J.*, 13(14):3302-11. (1994) (Exhibit 6).

Berger, M.S., et al., "Correlation of c-erbB-2 gene amplification and protein expression in human breast carcinoma with nodal status and nuclear grading." *Cancer Research*, 48(5):1238-43. (1988) (Exhibit 7).

Besson, A., et al., "PTEN/MMAC1/TEP1 in signal transduction and tumorigenesis." *Eur. J. Biochem.*, 263(3):605-11. (1999) (Exhibit 8).

Boney, C.M., et al., "The critical role of Shc in insulin-like growth factor-I-mediated mitogenesis and differentiation in 3T3-L1 preadipocytes." *Mol. Endocrinol.*, 14(6):805-13. (2000) (Exhibit 9).

Boylan, J.M., et al., "Uncoupling of hepatic, epidermal growth factor-mediated mitogen-activated protein kinase activation in the fetal rat." *J. Biol. Chem.*, 273(6):3784-90. (1998) (Exhibit 10).

Brown, N.S., et al., "Hypoxia and oxidative stress in breast cancer. Oxidative stress: its effects on the growth, metastatic potential and response to therapy of breast cancer." *Breast Cancer Res.*, 3(5):323-7. (2001) (Exhibit 11).

Buday, L. et al., "Epidermal growth factor regulates p21ras through the formation of a complex of receptor, Grb2 adaptor protein, and Sos nucleotide exchange factor." *Cell*, 73(3):611-20. (1993) (Exhibit 12).

Buday, L., et al., "Downregulation of the Ras activation pathway by MAP kinase phosphorylation of Sos." *Oncogene*, 11(7):1327-31. (1995) (Exhibit 13).

Bundred, N.J., et al., "Studies of epidermal growth factor receptor inhibition in breast cancer." *Endocr. Relat. Cancer* 8(3):183-9. (2001) (Exhibit 14).

Carraway, K.L., et al., "A neu acquaintance for erbB3 and erbB4: a role for receptor heterodimerization in growth signaling." *Cell*, 78(1):5-8. (1994) (Exhibit 15).

Carraway, K.L., et al., "Heregulin stimulates mitogenesis and phosphatidylinositol 3-kinase in mouse fibroblasts transfected with erbB2/neu and erbB3." *J. Biol. Chem.*, 270(13):711 1-6. (1995) (Exhibit 16).

Chen, D., et al., "SOS phosphorylation and disassociation of the Grb2-SOS complex by the ERK and JNK signaling pathways." *J. Biol. Chem.*, 271(11):6328-32. (1996) (Exhibit 17).

Clark, J.W., et al., "Effects of tyrosine kinase inhibitors on the proliferation of human breast cancer cell lines and proteins important in the Ras signaling pathway." *Int. J. Cancer*, 65(2):186-91 (1996) (Exhibit 18).

Cohen, G.B., et al., "Modular binding domains in signal transduction proteins." *Cell*, 80(2):237-48 (1995) (Exhibit 19).

Collins, L.R., et al., "Bifurcation of cell migratory ad proliferative signaling by adapter protein Shc." *J. Cell. Biol.*, 147(7): 1561-8. (1999) (Exhibit 20).

Culouscou, J.M., et al., "Characterization of a breast cancer cell differentiation factor that specifically activates the HER4/p180erbB4 receptor." *J. Biol. Chem.*, 268(25):18407-10. (1993) (Exhibit 21).

Dankort D., et al., "Multiple erbb-2/Neu phosphorylation sites mediate transformation through distinct effector proteins." *J. Biol. Chem.* 276(42):38921-8. (2001) (Exhibit 22).

Davol, P.A., et al., "Requirement for Shc phosphorylation in insulin-like growth factor-1 signaling to mitogen-activated protein kinase through the epidermal growth factor receptor in the prostrate adenocarcinoma cell line PC-3." *Proceedings AACR*, 42:5156. (2001) (Exhibit23).

Dickson, C., et al., "Tyrosine kinase signaling in breast cancer: fibroblast growth factors and their receptors." *Breast Cancer Res.*, 2(3):191-6. (2000) (Exhibit 24).

Dickson, R.B., et al., "Breast cancer: influence of endocrine hormones, growth factors and genetic alterations." *Adv. Exp. Med. Biol.*, 330:119-41. (1993) (Exhibit 25).

Dickson, R.B., et al., "Growth factors in breast cancer." *Endocr. Rev.*, 16(5):559-89. (1995) (Exhibit 26).

Dougall, W.C., et al., "The neu-oncogene: signal transduction pathways, transformation mechanisms and evolving therapies." *Oncogene*, 9(8):2109-23. (1994) (Exhibit 27).

Ennis, B.W., et al., "Anti-epidermal growth factor receptor antibodies inhibit the autocrine-stimulated growth of MDA-468 human breast cancer cells." *Mol. Endocrinol.*, 3(11):1830-8. (1989) (Exhibit 28).

Faisal, A., et al. "Serine/threonine phosphorylation of ShcA. Regulation of protein-tyrosine phosphatase-pest binding and involvement in insulin signaling." *J. Biol. Chem.*, 277(33): 30144-52. (2002) (Exhibit 29).

Feig, L.A., "Guanine-nucleotide exchange factors: a family of positive regulators of Ras and related GTPases." *Curr. Opin. Cell. Biol.*, 6(2):204-11. (1994) (Exhibit 30).

Filardo, E.J., et al., "Estrogen-induced activation of Erk-1 and Erk-2 requires the G protein-coupled receptor homolog, GPR30, and occurs via trans-activation of the epidermal growth factor receptor through release of HB-EGF." *Mol. Endocrinol.*, 14(10):1649-60. (2000) (Exhibit 31).

Goldhirsch, A., et al., "Meeting highlights: international consensus panel on the treatment of primary breast cancer. Seventh International Conference on Adjuvant Therapy of Primary Breast Cancer." *J. Clin. Oncol.*, 19(18):3817-27. (2001) (Exhibit 32).

Gotoh, N., et al., "The SH2 domain of She suppresses EGF-induced mitogenesis in a dominant negative manner." *Oncogene*, 11(12):2525-33. (1995) (Exhibit 33).

Gotoh, N., et al., "A novel pathway from phosphorylation of tyrosine residues 239/240 of Shc, contributing to suppress apoptosis by IL-3." *EMBO. J.*, 15(22):6197-204. (1996) (Exhibit 34).

Gotoh, N., et al., "Tyrosine phosphorylation sites at amino acids 239 and 240 of Shc are involved in epidermal growth factor-induced mitogenic signaling that is distinct from Ras/mitogen-activated protein kinase activation." *Mol. Cell. Biol.*, 17(4):1824-31. (1997) (Exhibit 35).

Gresham, J., et al., "Involvement of Shc in the signaling response of human prostrate tumor cell lines to epidermal growth factor." *Int. J. Cancer*, 77(6):923-7. (1998) (Exhibit 36).

Gu, J., et al., "Shc and FAK differentially regulate cell motility and directionality modulated by PTEN." *J. Cell. Biol.*, 146(2):389-403. (1999) (Exhibit 37).

Gu, H., et al., "New role for Shc in activation of the phosphatidylinositol 3-kinase/Akt pathway." *Mol. Cell. Biol.*, 20(19):7109-20. (2000) (Exhibit 38).

Hamilton, J.A., et al., "The expression profile for the tumor suppressor gene PTEN and associated polymorphic markers." *Br. J. Cancer*, 82(10):1671-6. (2000) (Exhibit 39).

Hashimoto, A., et al., "Shc regulates epidermal growth factor-induced activation of the JNK signaling pathway." *J. Biol. Chem.*, 274(29):20139-43. (1999) (Exhibit 40).

Hayes, D.F., et al., "Prognostic factors in breast cancer: current and new predictors of metastasis." *J. Mammary Gland Biol. Neoplasia*, 6(4):375-92. (2001) (Exhibit 41).

Hines, S.J., et al., "Coexpression of the c-kit and stem cell factor genes in breast carcinomas." *Cell. Growth Differ.*, 6(6):769-79. (1995) (Exhibit 42).

Hudziak, R., et al., "Increased expression of the putative growth factor receptor p185HER2 causes transformation and tumorigenesis of NIH3T3 cells." *Proc. Natl. Acad. Sci.*, 84:7159-63. (1987) (Exhibit 41).

Hynes, N., "Amplification and overexpression of the erbB-2 gene in human tumors: its involvement in tumor development, significance as a prognostic factor, and potential as a target for cancer therapy." *Seminars in Cancer Biology*, 4:19-26. (1993) (Exhibit 44).

Hynes, N.E. "Tyrosine kinase signaling in breast cancer." *Breast Cancer Res.*, 2(3):154-7. (2000) (Exhibit 45).
Irani, K., et al., "Mitogenic signaling mediated by oxidants in Ras-transformed fibroblasts." *Science*, 275(5306): 1649-52. (1997) (Exhibit 46).
Janes, P.W., et al., "Activation of the Ras signalling pathway in human breast cancer cells overexpressing erbB-2." *Oncogene*, 9(12):3601-8. (1994) (Exhibit 47).
Karin, M., et al., "Transcriptional control by protein phosphorylation: signal transmission from the cell surface to the nucleus." *Curr. Biol.*, 5(7):747-57. (1995) (Exhibit 48).
Li, L., et al., "Single-cell MALDI: a new tool for direct peptide profiling." *Trends Biotechnol.*, 18(4):151-60. (2000) (Exhibit 49).
Luttrell, D.K., et al., "Involvement of pp60c-src with two major signaling pathways in human breast cancer." *Proc. Natl. Acad. Sci. USA*, 91(1):83-7. (1994) (Exhibit 50).
Luttrell, L.M., et al., "G-protein-coupled receptors and their regulation: activation of the MAP kinase signaling pathway by G-protein-coupled receptors." *Adv. Second Messenger Phosphoprotein Res.*, 31:263-77. (1997) (Exhibit 51).
Matoskova, B., et al., "Constitutive phosphorylation of eps8 in tumor cell lines: relevance to malignant transformation." *Mol. Cell. Biol.*, 15(7):3805-12. (1995) (Exhibit 52).
McGuire, W., et al., "How to use prognostic factors in auxiliary node-negative breast cancer patients." *J. Natl. Cancer Inst.*, 82:1006-12. (1990) (Exhibit 53).
Meyer, S., et al., "Analysis of the role of the Shc and Grb2 proteins in signal transduction by the v-ErbB protein." *Mol. Cell. Biol.*, 14(5):3253-62. (1994) (Exhibit 54).
Migliaccio, E., et al., "Opposite effects of the p52shc/p46shc and p66shc splicing isoforms on the EGF receptor-MAP kinase-fos signaling pathway." *EMBO. J.*, 16(4):706-16. (1997) (Exhibit 55).
Migliaccio, E., et al., "The p66shc adaptor protein controls oxidative stress response and life span in mammals." *Nature*, 402(6759):309-13. (1999) (Exhibit 56).
Mitchell, P.J., et al., "Cloning and characterization of cDNAs encoding a novel non-receptor tyrosine kinase, brk, expressed in human breast tumours." *Oncogene*, 9(8):2383-90. (1994) (Exhibit 57).
Nemoto, S., et al., "Redox regulation of forkhead proteins through a p66shc-dependent signaling pathway." *Science*, 295(5564):2450-2. (2002) (Exhibit 58).
Nguyen, D.H., et al. "Urokinase-type plasminogen activator stimulates the Ras/Extracellular signal-regulated kinase (ERK) signaling pathway and MCF-7 cell migration by a mechanism that requires focal adhesion kinase, Src, and Shc. Rapid dissociation of GRB2/Sps-Shc complex is associated with the transient phosphorylation of ERK in urokinase-treated cells." *J. Biol. Chem.* 275(25):19382-8. (2000) (Exhibit 59).
Nolan, M.K., et al., "Differential roles of IRS-1 and SHC signaling pathways in breast cancer cells." *Int. J. Cancer*, 72(5):828-34. (1997) (Exhibit 60).
Normanno, N., et al., "Amphiregulin as an autocrine growth factor for c-Ha-ras- and c-erbB-2- transformed human mammary epithelial cells." *Proc. Natl. Acad. Sci. USA*, 91(7):2790-4. (1994) (Exhibit 61).
Okada, S., et al., "The 66-kDa Shc isoform is a negative regulator of the epidermal growth factor-stimulated mitogen-activated protein kinase pathway." *J. Biol. Chem.*, 272(44):28042-9. (1997) (Exhibit 62).
Panchamoorthy, G., et al. "p120cbl is a major substrate of tyrosine phosphorylation upon B cell antigen receptor stimulation and interacts in vivo with Fyn and Syk tyrosine kinases, Grb2 and Shc adaptors, and the p85 subunit of phosphatidylinositol 3-kinase." *J. Biol. Chem.* 271(6):3187-94. (1996) (Exhibit 63).
Pawson, T., et al., "Signal transduction and growth control in normal and cancer cells." *Curr. Opin. Genet. Dev.*, 4(1):1-4. (1994) (Exhibit 64).
Pawson, T., "Protein modules and signaling networks." *Nature*, 373(6515):573-80. (1995) (Exhibit 65).
Pelicci, G., et al., "A novel transforming protein (SHC) with an SH2 domain is implicated in mitogenic signal transduction." *Cell*, 70(1):93-104. (1992) (Exhibit 66).
Pelicci, G., et al., "The motogenic and mitogenic responses to HGF are amplified by the Shc adaptor protein." *Oncogene*, 10(8):1631-8. (1995) (Exhibit 67).
Pietrzkowski, Z., et al., "Inhibition of growth of prostatic cancer cell lines by peptide analogues of insulin-like growth factor." *Cancer Res.*, 53(5):1102-6. (1993) (Exhibit 68).
Ravichandran, K.S. "Signaling via Shc family adapter proteins." *Oncogene*, 20(44):6322-30. (2001) (Exhibit 69).
Rozakis-Adcock, M., et al., "Association of the Shc and Grb2/Sem5 SH2-containing proteins is implicated in activation of the Ras pathway by tyrosine kinases." *Nature*, 360(6405):689-92. (1992) (Exhibit 70).
Sasaoka, T., et al., "Evidence for a functional role of Shc proteins in mitogenic signaling induced by insulin, insulin-like growth factor-1, and epidermal growth factor." *J. Biol. Chem.*, 269(18):13689-94 (1994) (Exhibit 71).
Schechter, A.L., et al., "The neu oncogene: an erb-B-related gene encoding a 185,000-Mr tumour antigen." *Nature*, 312(5994):513-6. (1984) (Exhibit 72).
Scita, G., et al., "EPS8 and E3B1 transduce signals from Ras to Rac." *Nature*, 401(6750):290-3. (1999) (Exhibit 73).
Segatto, O., et al., "Shc products are substrates of erbB-2 kinase." *Oncogene*, 8(8):2105-12. (1993) (Exhibit 74).
Seger, R., et al., "The MAPK signaling cascade." *FASEB. J.*, 9(9):726-35. (1995) (Exhibit 75).
Sepp-Lorenzino, L., et al., "Signal transduction pathways induced by heregulin in MDA-MB-453 breast cancer cells." *Oncogene*, 12(8):1679-87. (1996) (Exhibit 76).
Singh, A., et al., "Insulin-like growth factor type I and insulin-like growth factor type II stimulate oestradiol-17 beta hydroxysteroid dehydrogenase (reductive) activity in breast cancer cells." *J. Endocrinol.*, 129(2):R5-8. (1991) (Exhibit 77).
Slamon, D.J., et al., "Human breast cancer: correlation of relapse and survival with amplification of the HER-2/neu oncogene." *Science*, 235:177-82. (1987) (Exhibit 78).
Songyang, Z., et al., "SH2 domains recognize specific phosphopeptide sequences." *Cell*, 72(5):767-78. (1993) (Exhibit 79).
Stern, D.F., "Tyrosine kinase signaling in breast cancer: ErbB family receptor tyrosine kinases." *Breast Cancer Res.*, 2(3):176-83. (2000) (Exhibit 80).
Stevenson, L.E., et al., "Constitutively tyrosine phosphorylated p52 Shc in breast cancer cells: Correlation with ErbB2 and p66 Shc expression." *Breast Cancer Res. Treat.*, 49(2):119-28. (1998) (Exhibit 81).
Stevenson, L.E., et al., "Shc dominant negative disrupts cell cycle progression in both G0/G1 and G2/M of ErbB2 positive breast cancer cells." *Cell. Growth & Differentiation*, 10(1):61-71. (1999) (Exhibit 82).
Sutherland, R.L., et al., "Cyclin gene expression and growth control in normal and neoplastic human breast epithelium." *J. Steroid Biochem. Mol. Biol.*, 47(1-6):99-106. (1993) (Exhibit 83).
Trusolino, L., et al., "A signaling adapter function for alpha6beta4 integrin in the control of HGF-dependent invasive growth." *Cell*, 107(5):643-54 (2001) (Exhibit 84).
Tuck, A.B., et al., "Coexpression of hepatocyte growth factor and receptor (Met) in human breast carcinoma." *Am. J. Pathol.*, 148(1):225-32. (1996) (Exhibit 85).
Ventura, A., et al., "The p66Shc longevity gene is silenced through epigenetic modifications of an alternative promoter." *J. Biol. Chem.*, 277(25):22370-6. (2002) (Exhibit 86).
Webster, M.A., et al., "Requirement for both Shc and phosphatidylinositol 3' kinase signaling pathways in polyomavirus middle T-mediated mammary tumorigenesis." *Mol. Cell. Biol.*, 18(4):2344-59. (1998). (Exhibit 87).
Whittal, R.M., et al., "Nanoliter chemistry combined with mass spectrometry for peptide mapping of proteins from single mammalian cell lysates." *Anal. Chem.*, 70(24):5344-7. (1998) (Exhibit 88).
Xie, Y., et al., "Tyrosine phosphorylation of Shc proteins and formation of Shc/Grb2 complex correlate to the transformation of N1H3T3 cells mediated by the point-mutation activated neu." *Oncogene*, 10(12):2409-13. (1995) (Exhibit 89).
Yarden, Y., "Biology of HER 2 and its importance in breast cancer." *Oncology*, 61 (Suppl 2):1-13. (2001) (Exhibit 90).

Zhang, X., et al. Tyrosine kinase signaling in breast cancer: insulin-like growth factors and their receptors in breast cancer. *Breast Cancer Res*,2(3):170-5. (2000) (Exhibit 91); and.

Zhao, H., et al., "Insulin receptor-mediated dissociation of Grb2 from Sos involves phosphorylation of Sos by kinase(s) other than extracellular signal-regulated kinase." *J. Biol. Chem.*, 273(20):12061-7. (1998) (Exhibit 92).

Davol, P.A., et al., "SHC Adaptor Proteins in Breast Cancer Prognosis: Novel Molecular Markers That Predict Aggressive Stage 1 Tumors", Proceedings of the Annual Meeting of the American Association for Cancer Research, New York, NY, vol. 43, p. 44, No. 221 (Mar. 2002).

Frackelton, A.R., et al., "p66 Shc and Tyrosine-Phosphorylated Shc in Primary Breast Tumors Identify Patients Likely to Relapse Despite Tamoxifen Therapy," *Breast Cancer Res.*, 8(6): p. R73 (Dec. 2006).

Wang, H-C., et al., "Future Prospects of Neoadjuvant Chemotherapy in Treatment of Primary Breast Caner", *Seminars in Surgical Oncology*, 12(1):59-66 (1996).

U.S. Appl. No. 10/687,396, filed Jan. 23, 2006, Office Action—Restriction Requirement.

U.S. Appl. No. 10/687,396, filed Feb. 23, 2006, Reply to Restriction Requirement.

U.S. Appl. No. 10/687,396, filed Mar. 27, 2006, Office Action.

U.S. Appl. No. 10/687,396, filed Sep. 29, 2006, Notice of Abandonment.

U.S. Appl. No. 11/511,073, filed Nov. 20, 2006, Preliminary Amendment.

U.S. Appl. No. 11/511,073, filed Feb. 12, 2007, Office Action—Restriction Requirement.

U.S. Appl. No. 11/511,073, filed Sep. 12, 2007, Notice of Abandonment.

U.S. Appl. No. 11/891,645, filed Feb. 11, 2008, Preliminary Amendment.

U.S. Appl. No. 11/891,645, filed Mar. 25, 2009, Office Action—Restriction Requirement.

U.S. Appl. No. 12/151,960, filed Aug. 4, 2008, Preliminary Amendment.

Nov. 30, 2005, Notification of Transmittal of the International Search Report or the Declaration, PCT/US2003/06035.

Aug. 15, 2008, Office Action, 2003228225.

Nov. 22, 2006, Communication pursuant to Rules 109 and 110 EPC, 03726003.1.

Dec. 15, 2005, Notification of Transmittal of the International Search Report and the Written Opinion of the International Searching Authority, or the Declaration, PCT/US2004/34430.

Apr. 27, 2006, Notification Concerning Transmittal of International Preliminary Report on Patentability, PCT/US2004/34430.

Nov. 25, 2008, Office Action, 2003-572357.

Apr. 28, 2006, Amendment, 2004 282598.

Mar. 11, 2008, Examiner's First Report, 2004 282598.

May 25, 2006, Communication pursuant to Rules 109 and 110 EPC, 04809980.8.

Nov. 3, 2006, Supplementary European Search Report (partial), 04809980.8.

Nov. 21, 2006, Communication from European Patent Office, 04809980.8.

Mar. 7, 2007, Notification of Transmittal of the International Search Report and the Written Opinion of the International Searching Authority, or the Declaration PCT/US2006/043852.

Mar. 7, 2007, Written Opinion of the International Searching Authority PCT/US2006/043852.

May 22, 2008, Notification Concerning Transmittal of International Preliminary Report on Patentability, PCT/US2006/043852.

Mar. 31, 2008, Entry into European Phase—Amended Claims, 06837361.2.

Jun. 18, 2008, Communication Pursuant to Rules 161 and 162 EPC, 06837361.2.

Oct. 20, 2008, Communication Pursuant to Article 94(3) EPC, 06837361.2.

Jun. 9, 2009, Notice of Loss of Rights Pursuant to Rule 112(1) EPC, 06837361.2.

U.S. Appl. No. 11/891,645, filed Sep. 25, 2009, Reply to Restriction Requirement.

Jul. 16, 2009, Official Action, 2,477,953.

Jun. 30, 2009, Office Action, 2003-572357.

Aug. 7, 2009, Response to Official Communication, 06837361.3.

U.S. Appl. No. 12/161,548, filed Nov. 27, 2009, Office Action—Restriction.

U.S. Appl. No. 11/891,645, filed Jan. 12, 2010, Office Action.

U.S. Appl. No. 12/151,960, filed Mar. 5, 2010, Office Action.

Mar. 9, 2010, Decision of Rejection, 2003-572357.

Huebner, K., et al., "Chromosome Locations of Genes Encoding Human Signal Transduction Adapter Proteins, Nck (NCK), Shc (SHC1), and Grb2 (GRB2)", *Genomics*, 22:281-287 (1994).

Salcini, A.E., et al., "Formation of Shc-Grb2 Complexes is Necessary to Induce Neoplastic Transformation by Overexpression of Shc Proteins", *Oncogene*, 9:2827-2836 (1994).

Wong, Nathalie, et al., "Positional Mapping for Amplified DNA sequences on 1q21-q22 in Hepatocellular Carcinoma Indicates Candidate Genes Over-Expression", *J. Hepatology*, 38:298-306 (2003).

U.S. Appl. No. 11/891,645, filed Sep. 3, 2010, Office Action (Final).

Bonati, A., et al., "Selective Expression and Constitutive Phosphorylation of SHC Proteins in the CD34+ Fraction of Chronic Myelogenous Leukemias," *Cancer Research* 68:728-732 (2000).

Crowe, et al., "Phosphorylation of the SHC Proteins on Tyrosine Correlates with the Transformation of Fibroblasts and Erythoroblasts by the v-Sea Tyrosine Kinase," *Oncogene* 9:537-544 (1994).

McGlade, J., et al., "Shc Proteins are Phosphorylated and Regulated by the v-Src and v-Fps Protein Tyrosine Kinases," *Proc. Natl. Acad. Sci.* 89:8869-8873 (1992).

Pelicci, G., et al., "Constitutive Phosphorylation of Shc Proteins in Human Tumors," *Oncogene* 11:899-907 (1995).

Yang, J., et al., "Tyrosine Phosphorylation of Shc Proteins in Normal CD34+ Progenitor Cells and Leukemic Cells," *Blood* 94:373-374 (1999).

Ma, X-J., et al., "A Two-Gene expression Ratio Predicts clinical outcome in Breast Cancer Patients Treated with Tamoxifen", *Cancer Cell*, 5:607-616 (Jun. 2004).

Purdom S., and Chen Q.M., "p66$^{Shc}$: at the Crossroad of Oxidative Stress and the Genetics of Aging", *Trends Mol. Med.*, 9(5):206-210 (May 2003).

Pellegrini, M., et al., "p66SHC: The Apoptotic Side of Shc Proteins", *Apoptosis*, 10(1):13-18 (2005).

Trinei, M., et al., "A p53-p66Shc Signalling Pathway Controls Intracellular Redox Status, Levels of Oxidation-Damaged DNA and Oxidative Stress-Induced Apoptosis", *Oncogene*, 21:3872-3878 (2002).

Pacini, S., et al., "p66SHC Promotes Apoptosis and Antagonizes Mitogenic Signaling in T Cells", *Mol. and Cell. Biol.*, 24(4):1747-1757 (Feb. 2004).

Fiucci, G., et al., "p66-Shc is expressed in Multidrug Resistant Breast Cancer Cells and Associates with Caveolin", *M. Biol. Of the Cell*, 10:67a, Abstract 386 (Nov. 1999).

Fiucci, G., et al., "Loss of Anchorage-Independent Growth and Reduced Invasiveness in Multidrug Resistant Breast Cancer Cells and Its Relationship to Expression of p66-Shc and Caveolin-1", *FASEB J.*, 15(4):A209, Abstract 195.1 (Mar. 7, 2001).

Jackson, J.G., et al., "Elevated Levels of p66 Shc are Found in Breast Cancer Cell Lines and Primary Tumors with High Metastatic Potential", *Breast Cancer Res. and Treatment*, 57(1):74, Abstract 274 (1999).

Tecce, R., et al., "Endothelin-1 Mitogenic Signaling in Human Ovarian Carcinoma Cells Involves Epidermal Growth Factor-Receptor and Shc Phosphorylation", *Proceedings of the American Assoc. for Cancer Res. Annual Meeting*, 38:551, Abstract 3695 (Mar. 1997).

Blum, R., et al., "Tailoring Ras-Pathway-Inhibitor Combinations for Cancer Therapy," *Drug Resistance Updates* 8:369-380 (2005).

Catalyst Oncology, Inc. Announces the introduction of the Shc Test for the Assessment of Risk in Gastric Cancer Patients, Profile Products People Publication News Publications Patients Professions, online at: http://web.archive.org/web/20061102103333/http://www.catalystoncology.com/news/12.html and http://web.archive.org/web/20070718100936/http://www.catalystoncology.com/news/12.html [retrieved on Aug. 20, 2010] (Sep. 21, 2005).

Song, R.X., et al., "The Role of Shc and Insulin-like Growth Factor 1 Receptor in Mediating the Translocation of Estrogen Receptor and to the Plasma Membrane", *Proc. Natl. Acad. Sci. USA*, 101:2076-2081 (2004).

Yukimasa S., et al., "Enhanced Expression of p46 Shc in the Nucleus and p52 Shc in the cytoplasm of Human Gastric Cancer", *Int. J. Oncol.*, 26:905-911 (2005).

U.S. Appl. No. 12/161,548, filed May 21, 2010, Response to Restriction Requirement.

U.S. Appl. No. 12/161,548, filed Jul. 20, 2010, Office Action.

U.S. Appl. No. 11/891,645, filed Jul. 12, 2010, Amendment.

Feb. 22, 2010, Supplemental Search Report, 03726003.1.

Apr. 13, 2010, Notice of Acceptance, 2003228225.

Apr. 30, 2010, Notice of Acceptance, 2003228225.

Jan. 15, 2010, Amendment & Remarks, 2,477,953.

Jul. 20, 2010, Request to Proceed to Examination and Arguments, 03726003.1.

Jun. 8, 2010, First Examination Report, 2006215651.

\* cited by examiner

Figure 8

[(Distribution of Stained Cells /2) + Intensity Score]/10
where distribution score ranges from 0 to 10 (0% to 100%)

Scoring System for Stain Intensity

0 = 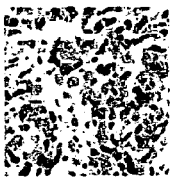 Background staining

1 =  Low level, punctate and non-uniform cellular staining pattern

2 =  Low level, punctate and uniform cellular staining pattern

3 =  Low level, evenly distributed cellular staining pattern

4 =  Moderate level, evenly distributed cellular staining pattern

5 = 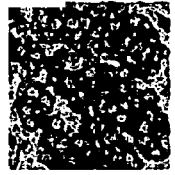 High level, evenly distributed cellular staining pattern

SHC PROTEIN-RELATED METHODS AND COMPOSITIONS FOR THE PROGNOSIS OF BREAST, PROSTATE AND OVARIAN CANCER

This application claims priority of U.S. Provisional Application No. 60/360,758, filed Mar. 1, 2002, the content of which is hereby incorporated by reference.

The invention described herein was made in the course of work under Department of Defense Breast Cancer Grant Numbers BC980415 and DAMD17-99-1-9363.

BACKGROUND OF THE INVENTION

Throughout this application, various publications are referenced by Arabic numerals in brackets. Full citations for these publications may be found listed at the end of the specification immediately preceding the claims. The disclosures of these publications in their entireties are hereby incorporated by reference into this application in order to more fully describe the state of the art as of the date of the invention described and claimed herein.

There is an urgent need for better prognostic indicators to guide the vigor and extent of surgical and adjuvant therapies of patients, especially those with early stage, node negative breast cancer [1], and those with early stage prostatic cancer. One breast-cancer marker that is associated with an aggressive phenotype is ErbB2, a member of the EGF family of growth factor receptors [2]. High expression of ErbB2 in node positive patients generally predicts a poor short term clinical outcome [3-5].

Recent studies on breast cancers also implicate additional growth-factor receptors such as other members of the EGF-receptor family; hepatocyte growth factor (HGF) and its receptor, c-Met; IGF-1 and its receptor; FGFs and their receptors; mammary-derived growth factor (MDGF-1 and its receptor); and non-receptor tyrosine kinases c-Src and Brk [reviewed in 6, and see 7, 8-10]. In addition to serving as markers for aggressive breast cancer, these growth factor receptors may have important functional roles in the aggressive phenotype. To the extent that this is true, measures of the sum total of growth-factor receptor signaling in tumor cells might provide the urgently needed accurate prognostic ability to guide surgical, radiation and chemoendocrine adjuvant therapy.

ErbB2 is a 185,000 molecular weight transmembrane glycoprotein that has an extracellular ligand binding domain and a cytoplasmic domain with tyrosine kinase activity [11]. What distinguishes ErbB2 from other receptor tyrosine kinases is that it is active when over expressed, even in the absence of any ligand [12]. For this reason, cells that over express high levels of ErbB2 protein proliferate in the absence of serum, and frequently appear transformed [13]. Mechanistically, over expression allows stable receptor dimers to form [14]. In contrast, most other growth-factor receptors must first bind their ligand before they can productively dimerize [15]. Dimerization activates the receptor tyrosine kinase. ErbB2 can also form active heterodimers with other family members after they have bound ligand [12]. For example, the EGF receptor-family members, HER-3 and HER-4 bind to HRG/NDF (heregulin and neu differentiation factor) ligand and activate ErbB2 through transmodulation [16-18]. Similarly, ErbB2 forms heterodimers with EGF receptors bound to EGF, thereby activating the ErbB2 tyrosine kinase [12].

The activated ErbB2 tyrosine kinase phosphorylates itself on specific tyrosine residues. Several "second messenger" proteins via their SH2 and PTB domains recognize and bind to the receptor's phosphorylated tyrosines [19-21]. Many of these proteins are then tyrosine phosphorylated by the receptor, and thereby activated, propagating the signaling cascade. One of these second messengers is the adapter protein, Shc, which appears to help transmit the signal to Ras, and thereby ultimately to DNA synthesis and cell proliferation (see FIG. 1) [22, 23] (and also reportedly signals to Myc [24, 25] and to PT 3' kinase [26]). The receptors phosphorylate tyrosine 317 in Shc, which in turn is recognized by Grb2-SOS complexes. As a result, SOS is translocated to the cellular membrane which appears to facilitate its ability to activate Ras [27-34]. It has been shown that signaling pathways to Ras are constitutively activated in many cell lines derived from breast cancers [35-38]. Further, several studies using microinjected antibodies to Shc, Shc antisense, and various Shc dominant-negative constructs have shown the dependence on a functional Shc of signaling from the EGF receptor, Her2/Neu, IGF-1 and HGF [8, 22, 39-42]. There are three isoforms of Shc: p66, p52 and p46 of 66, 52, and 46 kDa, respectively [21, 23, 43]. The p66 Shc isoform contains a unique N-terminal domain (CH2) not found in the p52 or p46 Shc isoforms [23]. In contrast to p52 and p46 Shc, p66 Shc does not activate the MAP kinase signaling cascade but rather actually inhibits the ability of growth factors to activate c-fos [44].

Currently the National Cancer Institute lists more than 95 open or planned clinical trials employing a myriad of tyrosine kinase inhibitors (TKI) specific for Her-2/neu, the EGF receptor or any of several other receptor and non-receptor tyrosine kineses. However, these trials in general are greatly hampered by the clinician's inability to predict which patients have tumors that are likely to respond to any single TKI or combination of TKIs.

SUMMARY OF THE INVENTION

This invention provides a method for determining whether a breast, prostate or ovarian tumor cell is aggressive, which method comprises determining the amount of p66-Shc and/or phosphorylated Shc present in the tumor cell, and comparing the amount(s) so determined to a known standard, thereby determining whether the tumor cell is aggressive.

This invention further provides a method for determining whether a breast, prostate or ovarian tumor cell is aggressive, which method comprises determining the ratio of p66-Shc to phosphorylated Shc and/or the ratio of phosphorylated Shc to p66-Shc in the tumor cell, and comparing the ratio(s) so determined to a known standard, thereby determining whether the tumor cell is aggressive.

This invention further provides a method for determining whether a breast, prostate or ovarian tumor in a subject is aggressive, which method comprises determining the amount of p66-Shc and/or phosphorylated Shc present in the cancerous cells of the tumor, and comparing the amount so determined to a known standard, thereby determining whether the tumor is aggressive.

This invention further provides a method for determining whether a breast, prostate or ovarian tumor in a subject is aggressive, which method comprises determining the ratio of p66-Shc to phosphorylated Shc and/or the ratio of phosphorylated Shc to p66-Shc present in the cancerous cells of the tumor, and comparing the ratio(s) so determined to a known standard, thereby determining whether the tumor is aggressive.

This invention further provides a method for determining whether a breast, prostate or ovarian tumor in a subject is aggressive, which method comprises determining the ratios of p66-Shc to phosphorylated Shc and/or the ratios of phosphorylated Shc to p66-Shc in each of a plurality of cancerous cells present in the tumor, and comparing the ratios so determined with a known standard, thereby determining whether the tumor is aggressive.

This invention further provides a method for determining whether a breast, prostate or ovarian tumor in a subject is aggressive, which method comprises determining the ratios of p66-Shc to phosphorylated Shc and/or the ratios of phosphorylated Shc to p66-Shc in each of a plurality of cancerous cells present in the tumor, and comparing the ratios so determined with a known standard, thereby determining whether the tumor is aggressive.

This invention further provides a method for determining, for a subject diagnosed as afflicted with a breast, prostate or ovarian tumor, the likelihood of the subject's suffering a recurrence of the tumor following primary treatment, which method comprises determining the amount of p66-Shc and/or phosphorylated Shc present in the cancerous cells of the tumor, and comparing the amount so determined to a known standard, thereby determining the likelihood of recurrence.

This invention further provides a method for determining, for a subject diagnosed as afflicted with a breast, prostate or ovarian tumor, the likelihood of the subject's suffering a recurrence of the tumor following primary treatment, which method comprises determining the ratio of p66-Shc to phosphorylated Shc and/or the ratio of phosphorylated Shc to p66-Shc present in the cancerous cells of the tumor, and comparing the ratio(s) so determined to a known standard, thereby determining the likelihood of recurrence.

This invention further provides a method for determining, for a subject diagnosed as afflicted with a breast, prostate or ovarian tumor, the likelihood of the subject's suffering a recurrence of the tumor following primary treatment, which method comprises determining the amounts of p66-Shc and/or phosphorylated Shc in each of a plurality of cancerous cells present in the tumor, and comparing the amounts so determined with a known standard, thereby determining the likelihood of recurrence.

This invention further provides a method for determining for a subject diagnosed as afflicted with a breast, prostate or ovarian tumor, the likelihood of the subject's suffering a recurrence of the tumor following primary treatment, which method comprises determining the ratios of p66-Shc to phosphorylated Shc and/or the ratios of phosphorylated Shc to p66-Shc in each of a plurality of cancerous cells present in the tumor, and comparing the ratios so determined with a known standard, thereby determining the likelihood of recurrence.

This invention further provides isolated antibodies that specifically bind to p66-Shc, and to phosphorylated Shc, and hybridomas that produce a monoclonal antibody that specifically binds to phosphorylated Shc, and a monoclonal antibody that specifically binds to phosphorylated Shc.

This invention further provides for a kit for performing the methods of this invention, comprising (a) a detectable antibody that specifically binds to p66-Shc, (b) a detectable antibody that specifically binds to phosphorylated Shc, (c) reagents for generating a known standard, and (d) instructions for use.

This invention further provides a method for producing a monoclonal antibody that specifically binds to p66-Shc comprising culturing the instant hybridoma, and recovering the monoclonal antibody so produced.

This invention further provides a method for producing a monoclonal antibody that specifically binds to phosphorylated Shc comprising culturing the instant hybridoma, and recovering the monoclonal antibody so produced.

This invention further provides a method for determining the likelihood that a tumor can be successfully treated using a tyrosine kinase inhibitor, which method comprises: (a) contacting a first sample of cells from the tumor with the tyrosine kinase inhibitor under conditions which, in the absence of the tyrosine kinase inhibitor, would permit the formation of tyrosine phosphorylated Shc in the sample; (b) determining the amount of tyrosine phosphorylated Shc present in the sample; and (c) comparing the amount of tyrosine phosphorylated Shc as determined in step (b) with the amount of tyrosine phosphorylated Shc present in a second sample of cells from the tumor which has not been contacted with the tyrosine kinase inhibitor, whereby a greater amount of tyrosine phosphorylated Shc present in the second sample relative to the first indicates a likelihood that the tumor can be successfully treated with the tyrosine kinase inhibitor.

Finally, this invention further provides a kit for performing the methods of this invention, comprising, in separate compartments, (a) a detectable antibody that specifically binds to tyrosine phosphorylated Shc, (b) reagents for measuring the amount of antibody bound to tyrosine phosphorylated Shc, and (c) instructions for use.

BRIEF DESCRIPTION OF THE FIGURES

FIG. 8. Scoring system for Immunohistochemical staining of PY-Shc.

DETAILED DESCRIPTION OF THE INVENTION

Definitions

Figure 1:
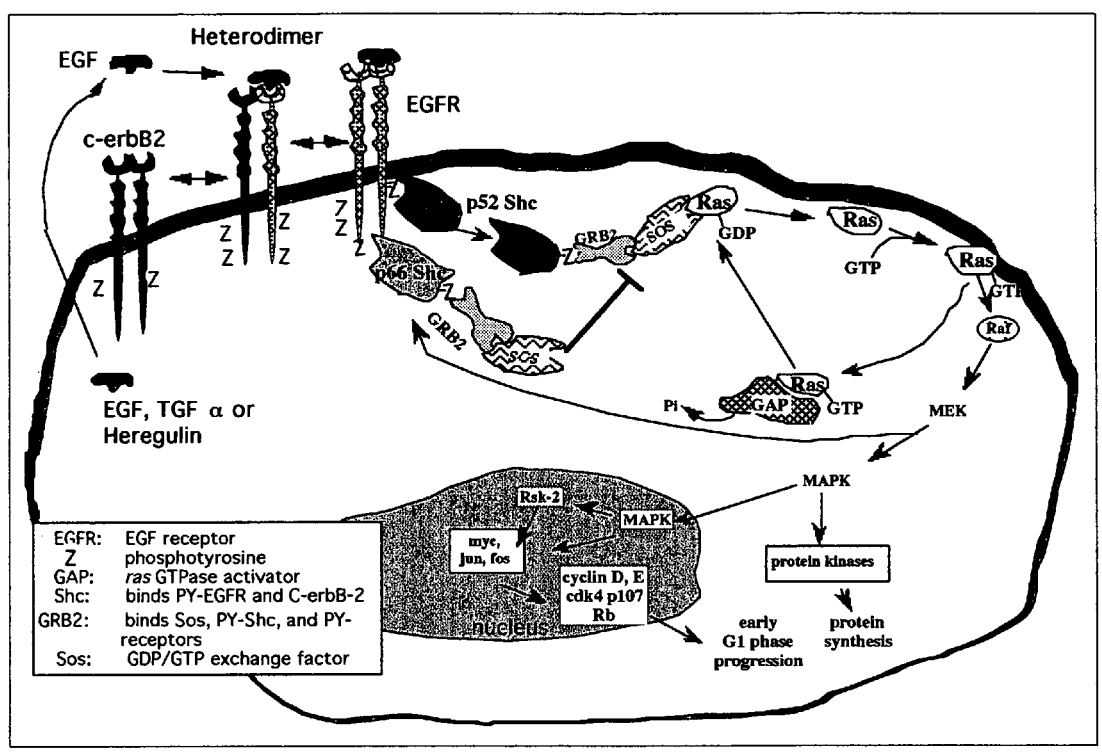
FIG. 1. Signaling Pathways Activate the Shc Adapter Protein (and feed-back inhibited by p66 Shc).

"Aggressive" shall mean, with respect to a tumor, having a predisposition to recur in a subject. Aggressive shall mean, with respect to a tumor cell, the origin of such cell from a tumor having a predisposition to recur.

"Amount", with respect to either p66-Shc or phosphorylated-Shc present in a cell, shall mean either (a) an absolute amount as measured in molecules, moles or weight per unit volume or cell, or (b) a relative amount as designated, for example, by a numerical rating from 0 to 5.

"Antibody" shall include, by way of example, both naturally occurring and non-naturally occurring antibodies. Specifically, this term includes polyclonal and monoclonal antibodies, and fragments thereof. Furthermore, this term includes chimeric antibodies and wholly synthetic antibodies, and fragments thereof (e.g., antigen-binding fragments).

"Known Standard" shall mean, in the context of this invention, one or more of an amount, ratio or distribution, as applicable, with regard to p66-Shc and phosphorylated Shc. A known standard preferably reflects such amount, ratio and/or distribution characteristic of an aggressive tumor and a non-aggressive tumor. Reagents for generating a known standard include, without limitation, tumor cells from a tumor known to be aggressive, tumor cells from a tumor known to be non-aggressive, and optionally labeled antibodies.

"P66-Shc" shall mean a 66 kD isoform of the adaptor protein designated "Shc".

"Phosphorylated Shc" shall mean the adaptor protein designated "Shc" having at least one of its amino acid residue side chains phosphorylated. Preferably, a tyrosine residue of Shc is phosphorylated ("tyrosine phosphorylated Shc"). Such residues include, for example, tyrosine residue 317.

"Primary Treatment" shall mean the initial treatment of a subject afflicted with a tumor. Primary treatments include, without limitation, surgery, radiation, hormone therapy, chemotherapy, immunotherapy, angiogenic therapy, and therapy via biomodulators.

"Recur" shall mean, with respect to a tumor, regrowth of cancerous cells from the tumor in a subject to whom primary treatment for the tumor has been administered.

"Subject" shall mean any animal, such as a mammal, and shall include, without limitation, mice and humans.

"Tumor cell" shall mean a cancerous cell within, or originating from, a tumor. Tumor cells are distinct from other, non-cancerous cells present in a tumor, such as vascular cells.

"Tyrosine kinase inhibitor" shall mean an agent that inhibits the function of a tyrosine kinase. Tyrosine kinase inhibitors include, without limitation, Gleevec (ST1571, Imatinab, cgp57148B), OSI-774, PP1, PP2, SU6656, SU4984, SU9518, SU5416, Genistein, Herbamycin A, PKC412, Tryphostins, CI-1033, PD168393, PD513032, AG126, AG1478, AG879, AG957, ZM39923, ZM449829, Iressa, ZD1839, Gefitinib, Emodin, Erbstatin, B46, Nigericin, PTK787 by Novartis, PKI116 by Novartis, Quinazolone family, Dianilinopthalimides, TK137, PDI166, CP-359,744, Geldanamycin, Erlotinib, Phenoxodiol, GW57216, ZD6474, UCN-01 and Lavendustin A.

Embodiments of the Invention

This invention provides a method for determining whether a breast, prostate or ovarian tumor cell is aggressive, which method comprises determining the amount of p66-Shc and/or phosphorylated Shc present in the tumor cell, and comparing the amount(s) so determined to a known standard, thereby determining whether the tumor cell is aggressive.

In one embodiment of the instant method, only the amount of p66-Shc is determined. In a further embodiment of the instant method, only the amount of phosphorylated Shc is determined. In another embodiment of the instant method, the amounts of both p66-Shc and phosphorylated Shc are determined.

This invention further provides a method for determining whether a breast, prostate or ovarian tumor cell is aggressive, which method comprises determining the ratio of p66-Shc to phosphorylated Shc and/or the ratio of phosphorylated Shc to p66-Shc in the tumor cell, and comparing the ratio(s) so determined to a known standard, thereby determining whether the tumor cell is aggressive.

In one embodiment of the instant methods, the tumor cell is a human tumor cell. In another embodiment of the instant methods, the tumor cell is obtained from a subject whose lymph nodes are free of tumor cells. In a further embodiment of the instant methods, the tumor cell is a breast tumor cell, a prostate tumor cell or an ovarian tumor cell.

In one embodiment of the instant methods, the determination step comprises the use of a detectable antibody that specifically binds to p66-Shc or phosphorylated Shc. In another embodiment of the instant methods, the determination step comprises the use of flow cytometry or immunohistochemistry. In a further embodiment of the instant methods, the tumor cell is isolated. In a further embodiment of the instant methods, the tumor cell is present within a tissue sample.

This invention further provides a method for determining whether a breast, prostate or ovarian tumor in a subject is aggressive, which method comprises determining the amount of p66-Shc and/or phosphorylated Shc present in the cancerous cells of the tumor, and comparing the amount so determined to a known standard, thereby determining whether the tumor is aggressive.

In one embodiment of the instant method, only the amount of p66-Shc is determined. In a further embodiment of the instant method, only the amount of phosphorylated Shc is determined. In another embodiment of the instant method, the amounts of both p66-Shc and phosphorylated Shc are determined.

This invention further provides a method for determining whether a breast, prostate or ovarian tumor in a subject is aggressive, which method comprises determining the ratio of p66-Shc to phosphorylated Shc and/or the ratio of phosphorylated Shc to p66-Shc present in the cancerous cells of the tumor, and comparing the ratio(s) so determined to a known standard, thereby determining whether the tumor is aggressive.

This invention further provides a method for determining whether a breast, prostate or ovarian tumor in a subject is aggressive, which method comprises determining the amounts of p66-Shc and/or phosphorylated Shc in each of a plurality of cancerous cells present in the tumor, and comparing the amounts so determined with a known standard, thereby determining whether the tumor is aggressive.

This invention further provides a method for determining whether a breast, prostate or ovarian tumor in a subject is aggressive, which method comprises determining the ratios of p66-Shc to phosphorylated Shc and/or the ratios of phosphorylated Shc to p66-Shc in each of a plurality of cancerous cells present in the tumor, and comparing the ratios so determined with a known standard, thereby determining whether the tumor is aggressive.

In one embodiment, the subject is human. In another embodiment, the subject's lymph nodes are free of tumor cells. In a further embodiment, the tumor cell is a breast tumor cell, a prostate tumor cell or an ovarian tumor cell.

In one embodiment, the determination step comprises the use of a detectable antibody that specifically binds to p66-Shc or phosphorylated Shc. In another embodiment, the determination step comprises the use of flow cytometry or immunohistochemistry. In a further embodiment, the tumor cell is present within a tissue sample.

This invention further provides a method of determining, for a subject diagnosed as afflicted with a breast, prostate or ovarian tumor, the likelihood of the subject's suffering a recurrence of the tumor following primary treatment, which method comprises determining the amount of p66-Shc and/or phosphorylated Shc present in the cancerous cells of the tumor, and comparing the amount so determined to a known standard, thereby determining the likelihood of recurrence.

In one embodiment of the instant method, only the amount of p66-Shc is determined. In a further embodiment of the instant method, only the amount of phosphorylated Shc is determined. In another embodiment of the instant method, the amounts of both p66-Shc and phosphorylated Shc are determined.

This invention further provides a method for determining, for a subject diagnosed as afflicted with a breast, prostate or ovarian tumor, the likelihood of the subject's suffering a recurrence of the tumor following primary treatment, which method comprises determining the ratio of p66-Shc to phosphorylated Shc and/or the ratio of phosphorylated Shc to p66-Shc present in the cancerous cells of the tumor, and comparing the ratio(s) so determined to a known standard, thereby determining the likelihood of recurrence.

This invention further provides a method for determining, for a subject diagnosed as afflicted with a breast, prostate or ovarian tumor, the likelihood of the subject's suffering a recurrence of the tumor following primary treatment, which method comprises determining the amounts of p66-Shc and/or phosphorylated Shc in each of a plurality of cancerous cells present in the tumor, and comparing the amounts so determined with a known standard, thereby determining the likelihood of recurrence.

This invention further provides a method for determining for a subject diagnosed as afflicted with a breast, prostate or ovarian tumor, the likelihood of the subject's suffering a recurrence of the tumor following primary treatment, which method comprises determining the ratios of p66-Shc to phosphorylated Shc and/or the ratios of phosphorylated Shc to p66-Shc in each of a plurality of cancerous cells present in the tumor, and comparing the ratios so determined with a known standard, thereby determining the likelihood of recurrence.

In one embodiment, the subject is human. In another embodiment, the subject's lymph nodes are free of tumor cells. In a further embodiment, the tumor cell is a breast tumor cell, a prostate tumor cell or an ovarian tumor cell.

In one embodiment, the determination step comprises the use of a detectable antibody that specifically binds to p66-Shc or phosphorylated Shc. In another embodiment, the determination step comprises the use of flow cytometry or immunohistochemistry. In a further embodiment, the tumor cell is present within a tissue sample. In a further embodiment, the primary treatment comprises a treatment selected from the group consisting of surgery, radiation, hormone therapy and chemotherapy.

This invention further provides an isolated antibody that specifically binds to p66-Shc, and an isolated antibody that specifically binds to phosphorylated Shc.

In one embodiment, the antibody is polyclonal. In another embodiment, the antibody is monoclonal. In a further embodiment, the antibody is labeled with a detectable moiety. In a further embodiment, the detectable moiety is a fluorescent label, a radioactive atom, a chemiluminescent label, a paramagnetic ion, biotin or a label which can be detected through a secondary enzymatic or binding step. In one embodiment, the antibody is the monoclonal antibody produced by hybridoma having ATCC Accession No. PTA-4109.

This invention further provides a hybridoma that produces a monoclonal antibody that specifically binds to p66-Shc. In one embodiment, the hybridoma has ATCC Accession No. PTA-4109. This invention further provides a hybridoma that produces a monoclonal antibody that specifically binds to phosphorylated Shc.

This invention further provides a kit for performing the instant methods, comprising (a) a detectable antibody that specifically binds to p66-Shc, (b) a detectable antibody that specifically binds to phosphorylated Shc, (c) reagents for generating a known standard, and (d) instructions for use.

This invention further provides a method for producing a monoclonal antibody that specifically binds to p66-Shc comprising culturing the instant hybridoma, and recovering the monoclonal antibody so produced.

This invention further provides a method for producing a monoclonal antibody that specifically binds to phosphorylated Shc comprising culturing the instant hybridoma, and recovering the monoclonal antibody so produced.

This invention further provides a method for determining the likelihood that a tumor can be successfully treated using a tyrosine kinase inhibitor, which method comprises: (a) contacting a first sample of cells from the tumor with the tyrosine kinase inhibitor under conditions which, in the absence of the tyrosine kinase inhibitor, would permit the formation of tyrosine phosphorylated Shc in the sample; (b) determining the amount of tyrosine phosphorylated Shc present in the sample; and (c) comparing the amount of tyrosine phosphorylated Shc as determined in step (b) with the amount of tyrosine phosphorylated Shc present in a second sample of cells from the tumor which has not been contacted with the tyrosine kinase inhibitor, whereby a greater amount of tyrosine phosphorylated Shc present in the second sample relative to the first indicates a likelihood that the tumor can be successfully treated with the tyrosine kinase inhibitor.

In one embodiment of the instant method, the tumor is a breast tumor, a prostate tumor, or an ovarian tumor. In another embodiment, the sample of cells from the tumor is obtained from a subject whose lymph nodes are free of tumor cells. In another embodiment, the subject is human. In another embodiment, the tumor cell is a breast tumor cell, a prostate tumor cell or an ovarian tumor cell.

In one embodiment, determining the amount of tyrosine phosphorylated Shc comprises the use of a detectable antibody that specifically binds to tyrosine phosphorylated Shc. In a further embodiment, the antibody is detectably labeled. In another embodiment, determining the amount of tyrosine phosphorylated Shc comprises the use of flow cytometry or immunohistochemistry. In a further embodiment, the sample of tumor cells is present within a tissue sample.

This invention further provides a kit for performing the instant method, comprising, in separate compartments, (a) a detectable antibody that specifically binds to tyrosine phosphorylated Shc, (b) reagents for measuring the amount of antibody bound to tyrosine phosphorylated Shc, and (c) instructions for use.

It is noted that each of the various embodiments set forth above with respect to the instant methods also applies, mutatis mutandis, to the instant kits.

This invention is illustrated in the Examples section which follows. This section is set forth to aid in an understanding of the invention but is not intended to, and should not be construed to limit in any way the invention as set forth in the claims which follow thereafter.

EXAMPLES

Example 1

Materials and Methods

In a 12-year, retrospective study of clinical outcome (with at least a 5 year follow-up) of breast cancer patients in the Roger Williams Cancer Center database and tumor registry, a 10% mortality associated with disease recurrence was observed in patients diagnosed with Stage 1 breast cancer (n=212 patients). Accordingly, there is an evident need for molecular markers that may differentiate aggressive, early-stage breast cancers from less invasive lesions and thus guide surgical and adjuvant treatment options. Immunohistochemical staining of phosphorylated Shc (PY-Shc: an activated, adaptor protein that facilitates tyrosine kinase signaling and tumorigenesis) and p66-Shc (a Shc isoform that inhibits this signaling cascade) in 98 archival, formalin-fixed, diagnostic breast tumor biopsies (Stage 0 to Stage 4 patients) demonstrated a positive linear correlation between the ratio of PY-Shc to p66-Shc staining intensity in regard to patient stage (®=0.4; $p<0.0001$); with high PY-shc/low p66-Shc corresponding to advanced disease stage at the time of diagnosis. When the PY-Shc to p66-Shc ratio was analyzed in primary tumors from Stage 1 breast cancer patients and then retrospectively compared to patient outcome (5 yr follow-up), the ratio for randomly selected tumors from patients with no disease recurrence (0.66±0.03; n=30) was significantly lower compared to patients with disease recurrence (0.90±0.07; n=8) ($p<0.005$). These studies suggest that the PY-Shc to p66-Shc ratio may serve as a viable prognostic marker for identifying aggressive, early stage breast cancers.

To begin to address the functional roles of ErbB2 and other over-expressed growth-factor receptors in breast-cancer, it was asked whether the signaling pathway through Shc was constitutively active. A strong positive correlation between the levels of tyrosine-phosphorylated p52 Shc and the levels of ErbB2 ($r=0.91$; $p<0.002$) was found. Three breast-cancer cell lines, MCF-7, MDA-MB-468 and ZR-75-1, which express low to moderate levels of ErbB2 but do have autocrine EGF/TGF-α loops [45, 46] or stem-cell factor autocrine loops [47], displayed moderately elevated levels of tyrosine-phosphorylated Shc (PY-Shc). HBL-100 and Hs-578Bst, non-transformed mammary epithelial cell lines, evidenced little PY-Shc [38]. Thus the levels of PY-p52 Shc in breast cancer cells appear to be an excellent indicator of overall growth-factor receptor activity, and thus might be a useful marker for poor breast cancer prognosis.

Unexpectedly, although all cell lines had comparable total amounts of p52 and p46 Shc, the amount of the inhibitory Shc isoform, p66, was inversely related to the level of ErbB2 expression (®=-0.86, p=0.0013) [38], and similarly was inversely related to the levels of ErbB2 activation, PY-p52 Shc, and to the level of dependence on the PY-p52 Shc pathway for proliferation. This suggested the tantalizing possibility that p66 Shc functions as an anti-oncogene or a tumor suppressor for breast cancers that depend on the PY-p52/p46 pathway to activate MAP kinase, c-fos, and perhaps c-Myc and PI3' Kinase. Indeed, it was recently found that forcing breast cancer cells to express p66 Shc strongly inhibits their tumorgenicity. Thus, low cellular levels of p66 Shc may be a useful marker for poor breast cancer prognosis.

Because the above mentioned, considerable evidence implicated several activated growth-factor signaling systems in breast cancers, and because a vital step common to each of these signaling systems is tyrosine phosphorylation (activation) of the adapter protein, Shc, it was hypothesized that activated Shc would be a useful indicator of poor clinical prognosis—more useful than ErbB2 over expression inasmuch as Shc will be activated not only in breast cancers harboring active ErbB2, but also in breast cancers which may be driven to proliferate by other tyrosine kinases such as the IGF-1 receptor, c-Met, and other EGF receptor family members.

Furthermore, because of the finding of a strong negative correlation between the cellular levels of a putative anti-oncogenic isoform of Shc, p66, compared to cellular levels PY-p52 Shc, it was also hypothesized that low cellular levels of p66 Shc, especially when coupled with high cellular levels of PY-Shc, would be a useful indicator for poor clinical prognosis.

Moreover, Shc tyrosine phosphorylation and p66 Shc inhibitory effects occur at an early step in growth-factor signaling cascades. Many early-stage breast cancers that are ultimately destined to become aggressive disease may display elevated levels of PY-Shc, even though downstream signaling through the MAP kinase (Erk-1/2) cascade, proliferation and other prognostic markers may still remain low. Consistent with this notion, there are many examples emerging where growth-factor receptors and Shc are activated but Erk-1/2 are not [48-51]. Thus, high relative amounts of PY-Shc/p66 Shc may be especially useful indicators of poor prognosis in women with early stage/node negative breast cancers. Indeed, as described below, this has been found to be true.

Antisera and Monoclonal Antibody Development

Rabbit Antibodies to PY [317]-Shc: New Zealand White Rabbits were Immunized with an N-Acetylated Tyrosine-Phosphorylated Shc Peptide Following given direction, Research Genetics (Huntsville, Ala.) synthesized N-acetyl-LeuPheAspAspProSer ([P]Tyr) ValAsnValGlnAsnLeuCys (SEQ ID NO: 1) (corresponding to human Shc amino acids 311 to 323, with an added cysteine C-terminus to facilitate maleimide coupling to the carrier protein, Keyhole Limpet haemocyanin (KLH)). The peptide-KLH was emulsified in Freund's Adjuvant and a total of 0.1 mg of peptide was injected into multiple dorsal sites of New Zealand White rabbits. Rabbits were rechallenged at 2-week intervals, bled one week after each challenge and terminated after the 10th week. Antibodies were purified by immunospecific affinity chromatography on the Shc phosphopeptide (covalently attached to an Ultralink Iodoacetyl matrix (Pierce), according to the manufacturer's directions), eluting with 0.23 M glycine Hcl buffer, pH 2.8, into one-tenth volume of 1M TRIS (Sigma, St. Louis), pH 9.0 to neutralize the pH. Antibodies from all immunized rabbits demonstrated high titer by ELISA assay against the immunizing peptide (data not shown) and clear specificity for Sch by immunoprecipitation (data not shown). Antibodies from rabbit #58 appeared to recognize only the tyrosine phosphorylated form of Shc. Suggesting that the little of the #58's specificity was directed to phosphotyrosine alone, #58 did not immunoprecipitate other PY-proteins such as ErbB-2. In addition, 1 mM sodium phenyl phosphate, a potent phosphotyrosine analog, had minimal effect on the ability of #58 to immunoprecipitate Shc, while in contrast, the 1 mM sodium phenyl phosphate completely blocked the ability of the 4G10 monoclonal antibody to phosphotyrosine to immunoprecipitate PY-Shc and other PY-proteins such as PY-ErbB-2 and PY-EGF-receptor.

Figure 2:
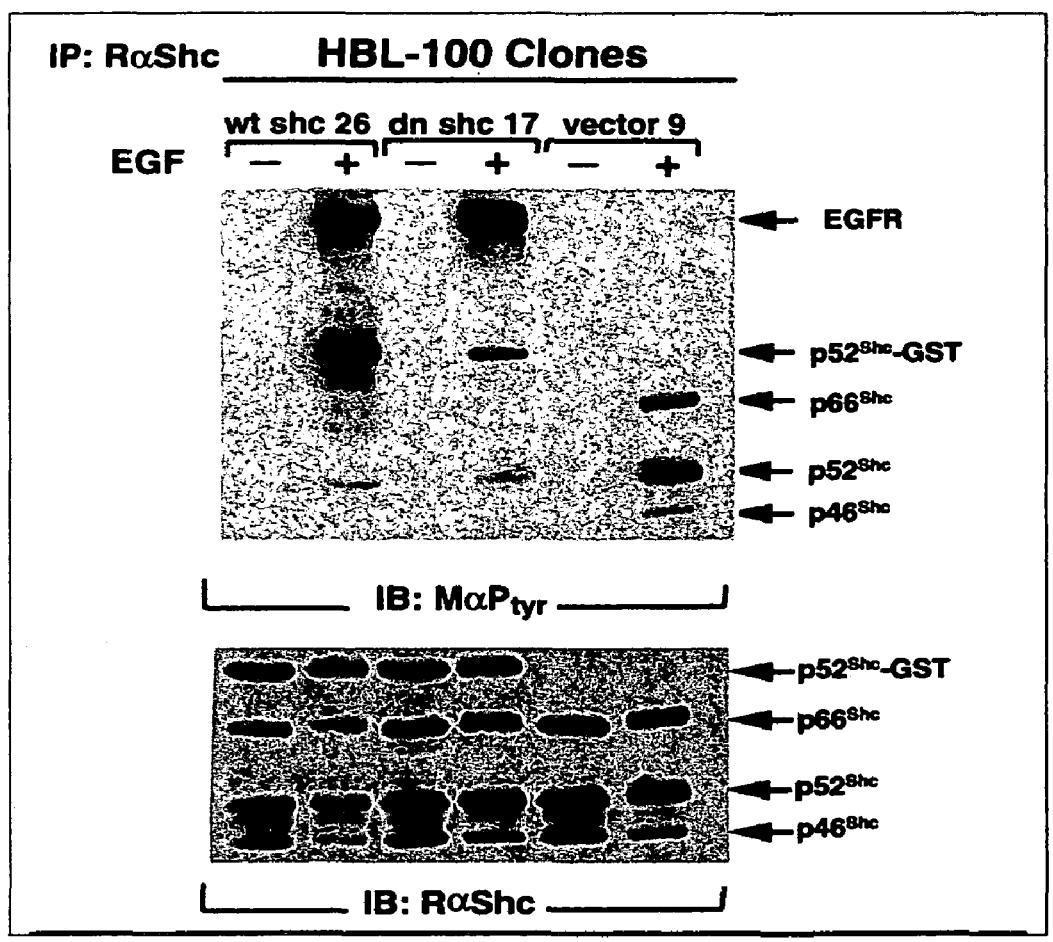
FIG. 2. HBL-100 clones transfected to constitutively express a wild-type p52Shc-Gst fusion protein (wt Shc 26) or a dominant-negative Ty317-mutant p52Shc-Gst fusion protein (dn Shc 17) demonstrate an increase in phosphorylation of tyrosine residues (317 and/or 239/240) on the fusion protein compared to endogenous Shc proteins.
Figure 3:
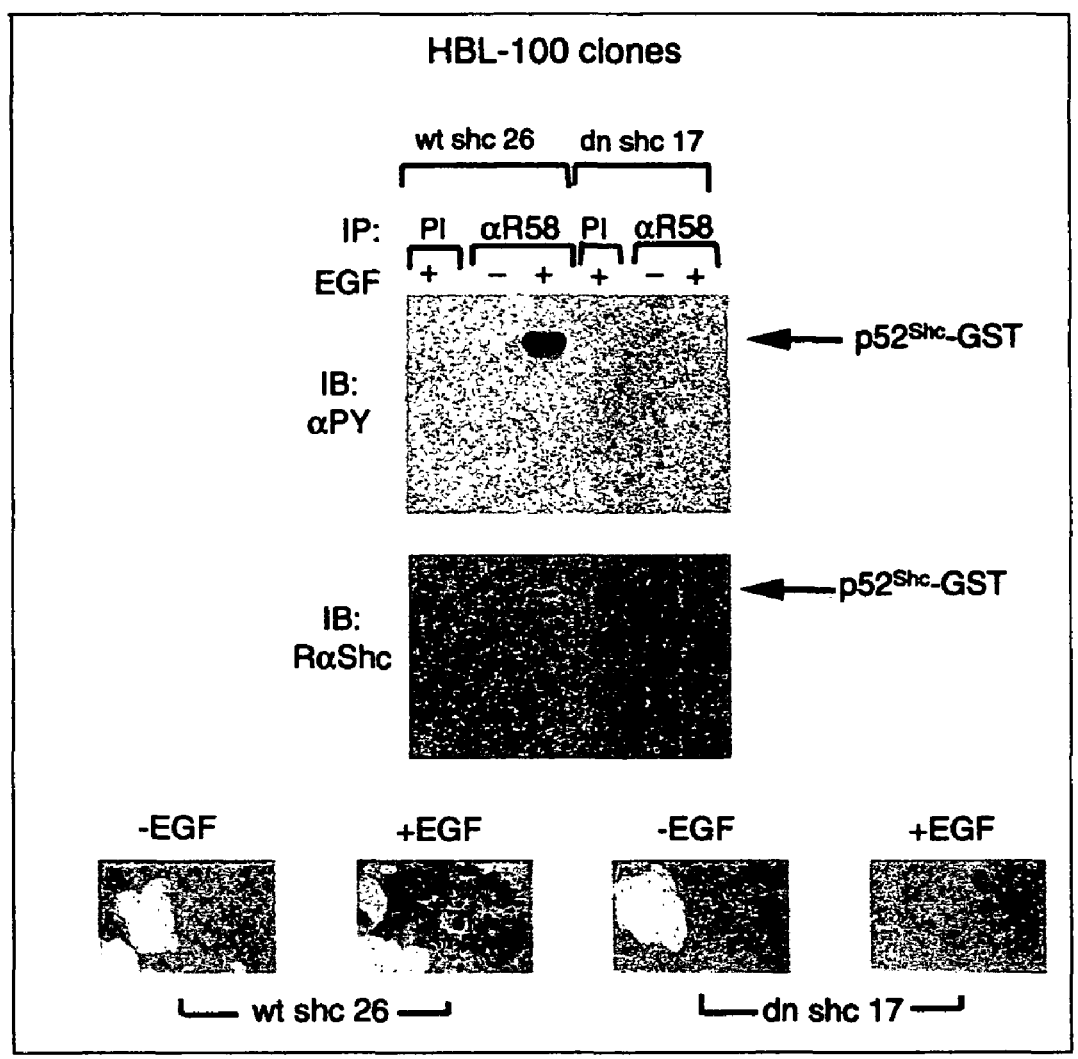
FIG. 3. R58 antibodies are specific for the phosphorylated tyrosine 317 residue of the Shc protein. Absence of Shc detection in EGF-non-stimulated wt shc 26 clones indicates that αR58 recognizes only the activated, tyrosine phosphorylated form of Shc. Furthermore, the inability of αR58 to detect Shc in EGF-stimulated on shc 17 clones, which lack only the tyrosine (317) phosphorylation site (see FIG. 2 for relative expression levels of dnShc in these cells), indicates that αR58 is not directed to phosphotyrosine alone.

This antibody's fine specificity was further assessed, first by Western blotting. For this purpose, HBL-100 breast epithelial cell lines were used that had been engineered to express either a wild type GST-human recombinant p52 Shc fusion protein (clone 26), a dominant negative GST-human recombinant p52 Shc fusion protein in which the 317 tyrosine had been mutated to a phenylalanine (clone 17), or an empty vector control (clone 9) [42]. As can be seen in FIG. 2, the expression of either the wt-Shc or the dn-Shc nearly completely blocked the ability of EGF to induce tyrosine phosphorylation of the endogenous p46, p52, and p66 Shc proteins. Instead in response to EGF, the wild type GST-Shc is heavily tyrosine phosphorylated (on residues 239 and 317) and the dn-Shc is lightly tyrosine phosphorylated (only on residue 239, since its 317 tyrosine residue has been mutated to a phenylalanine), and both of these expressed recombinant Shc proteins are tightly associated with EGF-induced tyrosine phosphorylated EGF receptor. These cells, then, were excellent prototypes to examine the fine specificity of the rabbit #58 antibody by immunoprecipitation and by immunocytochemistry. For, if the rabbit #58 antibody is indeed specific for PY317 Shc, it would be expected to only immunoprecipitate the tyrosine phosphorylated wt-GST-Shc from EGF-stimulated clone 26 cells. Indeed, this was the case (FIG. 3). The rabbit #58 antibody precipitated the tyrosine (239,317) phosphorylated wt-GST-Shc protein from EGF-stimulated clone 26 cells, but did not precipitate the tyrosine (239)-phosphorylated dn-GST-ShcY317F protein from clone 17 cells. Various controls showed that the rabbit #58 binding could be completely inhibited by the immunizing peptide, and that the antibody did not bind to other proteins that had been tyrosine phosphorylated in response to EGF. Importantly, the rabbit #58 antibodies showed similar specificity for PY317 Shc by immunocytochemical staining of EGF-stimulated clone 26 and clone 17 cells (FIG. 3, lower panels).

The determination of whether the rabbit #58 antibody to PY-Shc would positively stain breast cancer cell lines that was known to contain PY-Shc from earlier immunoblotting experiments was needed. All of the cell lines that contained significant levels of PY-Shc by immunoblotting also exhibited strong immunocytochemical staining with rabbit #58 antibody (data not shown). In contrast, a non-transformed breast epithelial cell line, Hs-578Bst, and the single breast cancer cell line, MDA-MB-231, that lack significant levels of tyrosine phosphorylated Shc by immunoblotting, also fail to stain with the PY-Shc specific rabbit #58 antibody.

Figure 4:
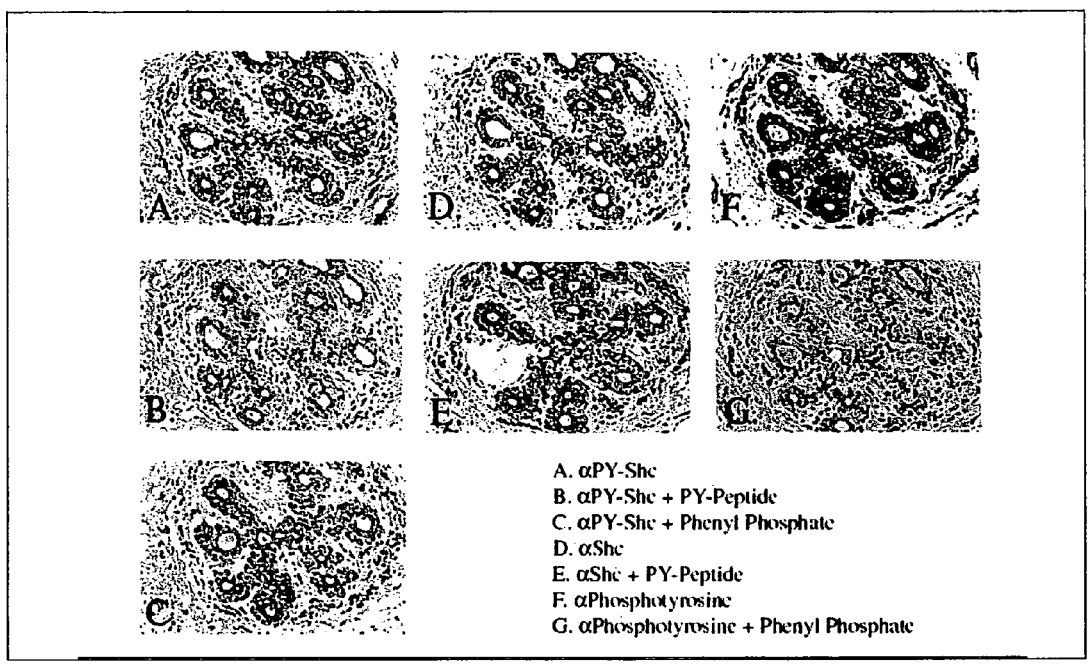
FIG. 4. Immunohistochemical specificity of the phospho-specific antibodies to Shc and the p66-isoform specific antibodies to Shc. Sections from a paraffin-embedded, formalin-fixed breast cancer were stained in the Upper Panel with anti-PY-Shc (first column), anti-Shc protein (second column), and anti-PY (third column) in the absence or presence of competing PY-Shc peptide or the phosphotyrosine analog, phenyl phosphate, as indicated. In the Lower Panel, sections from a different specimen were stained with pre-immune immunoglobulin (Pre-Immune) or our rabbit antibody specific for p66 Shc (anti-p66 She).

The characterization was extended to immunohistochemical staining of archival, formalin-fixed, paraffin-embedded specimens. The specificity and usefulness of #58 PY-Shc antibodies in immunohistochemical staining was evaluated in sections of human breast adenocarcinoma (FIG. 4). Anti-PY-Shc stained the cancerous glandular tissue strongly (FIG. 4A), and as expected, staining was markedly inhibited by the immunizing PY-peptide (FIG. 4B), but only slightly inhibited by a partial antagonist, the phosphotyrosine analog, phenyl phosphate (FIG. 4C). In contrast, staining with pan-Shc antibody (directed to the protein backbone) was not inhibited by the PY-peptide (FIG. 4D,E), while, in contrast, pure anti-phosphotyrosine staining was completely inhibited by phenyl phosphate (FIG. 4F,G). Details of the immunohistochemical evaluation of breast cancers are provided below.

Rabbit Antibodies Specific for p66Shc (CH2 Domain)

Research Genetics was contracted to synthesize a hydrophilic peptide, SerGlySerThrProProGluGluLeuProSerProSerAlaSerSerLeu (SEQ ID NO:2), derived from the p66 Shc$_{1-110}$ CH2 domain. The peptide was coupled to the carrier protein, KLH, and used to immunize New Zealand White rabbits, employing a standard, 10-week immunization/Challenge protocol, as detailed above. The antisera collected at 10 weeks were tested for reactivity against the immunizing peptide in a solid phase ELISA. Antisera from rabbit #405 reacted with the immunizing peptide (titer of about 1/5000). The peptide-specific antibodies were affinity purified from rabbit #405 antisera using the immunizing peptide (covalently attached to the Ultralink Iodoacetyl matrix (Pierce), according to the manufacturer's directions), eluting with 0.23 M glycine Hcl buffer, pH 2.8, into one-tenth volume of 1M TRIS (Sigma, St. Louis), pH 9.0 to neutralize the pH. The purified antibody was tested for its ability to recognize human recombinant GST-p66 Shc CH2 domain (a fusion protein comprised of GST and the first 110 amino acids of p66 Sch the amino acids unique to p66 Shc compared to the p52 Shc isoform). The human recombinant Gst-p66 Sch$_{1-110}$ bacterial expression vector was obtained from Prof. Pelicci, in Milan, Italy. We expressed this protein in E. coli, and affinity purified it using a glutathione affinity matrix. SDS PAGE analysis and Coomassie blue staining revealed that the purified protein consisted of three major bands near the predicted molecular weight of the fusion protein, along with a faster migrating band, and a much slower migrating group of minor bands. Immunoblotting with antibodies to GST revealed that all of the bands contained GST. The rabbit #405 antibodies reacted with all but the fastest migrating species (data not shown). This was interpreted to mean that the fastest moving band contains only GST (or GST and a small piece of p66CH2 that does not contain the p66 epitope used for immunization). The other bands near the predicted molecular size likely are the intact GST-p66 Shc CH2 fusion protein and the proteolytic clips of this protein, while the highest molecular weight proteins are almost certainly dimers of GST-p66Shc CH2 and its proteolytic fragments caused by GST mixed disulfide reactions (unpublished observations). Thus, not only did the antisera raised against the small CH2 peptide recognize the whole CH2 domain, but it can do this on immunoblots and appeared relatively specific (it did not react with the GST-only band).

Figure 5:
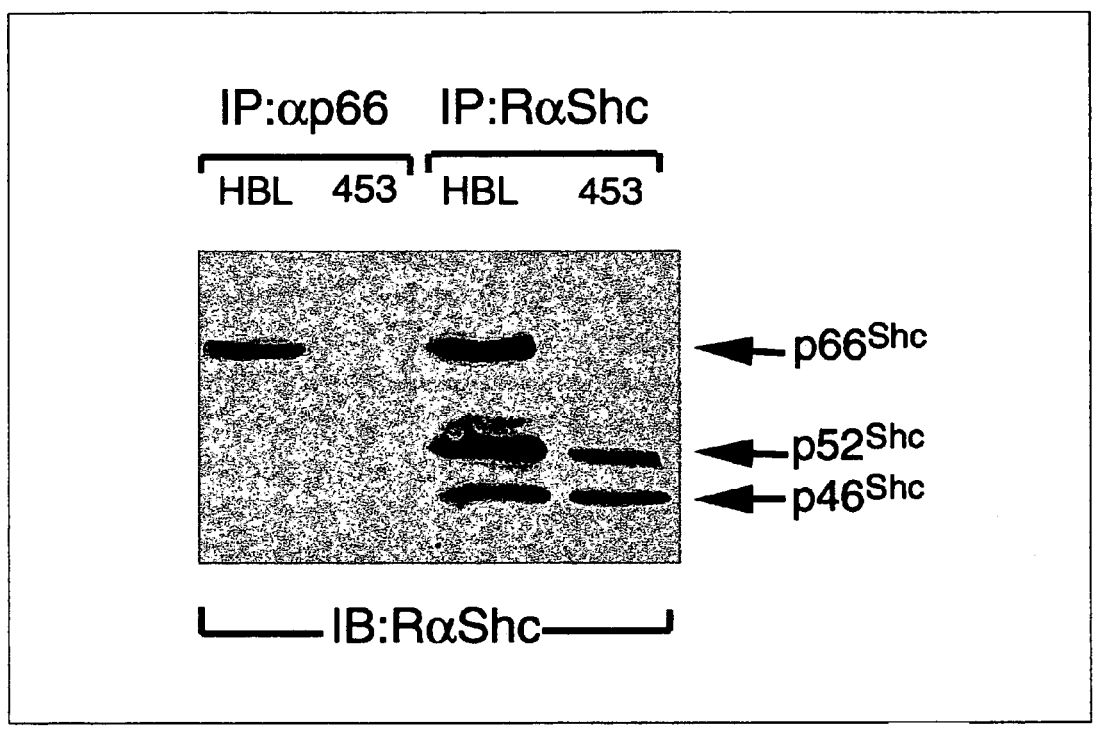
FIG. 5. Rabbit antibody #405 Specifically Immunoprecipitates the 66-kDaShc Isoform. The Rabbit antibody #405 (lanes IP:α66) immunoprecipitates p55 Shc from detergent extracts of HBL-100 cells, but not from the MDA-MB-453 cells that lack expression of the 66-kDa Shc isoform. In the lanes labeled IP-RαShc, all She proteins were immunoprecipitated using a pan-Shc-specific antibody. The blot was probed with the pan-Shc specific antibody.

To further test the specificity of the rabbit #405 antibody it was asked if it would specifically immunoprecipitate p66 Shc. To test this, we took advantage of our prior findings (see FIG. 2), that the breast epithelial cell line, HBL-100, contains normal levels of p66 Shc, comparable to levels of p52 Shc, while the breast cancer cell line, MDA-MB-453, lacks detectable p66 Shc. The rabbit #405 antibody cleanly and clearly precipitated only the p66 Shc protein (FIG. 5). Fine specificity analysis suggests that the rabbit polygonal antibodies preferentially recognize the dephospho (serine 36)-form of the p66 Shc protein.

Immunocytochemical staining of the HBL-100 and MDA-MB-453 cells revealed that the rabbit #405 antibody also could specifically detect p66 Shc in the HBL-100 cells (data not shown).

Figure 6:
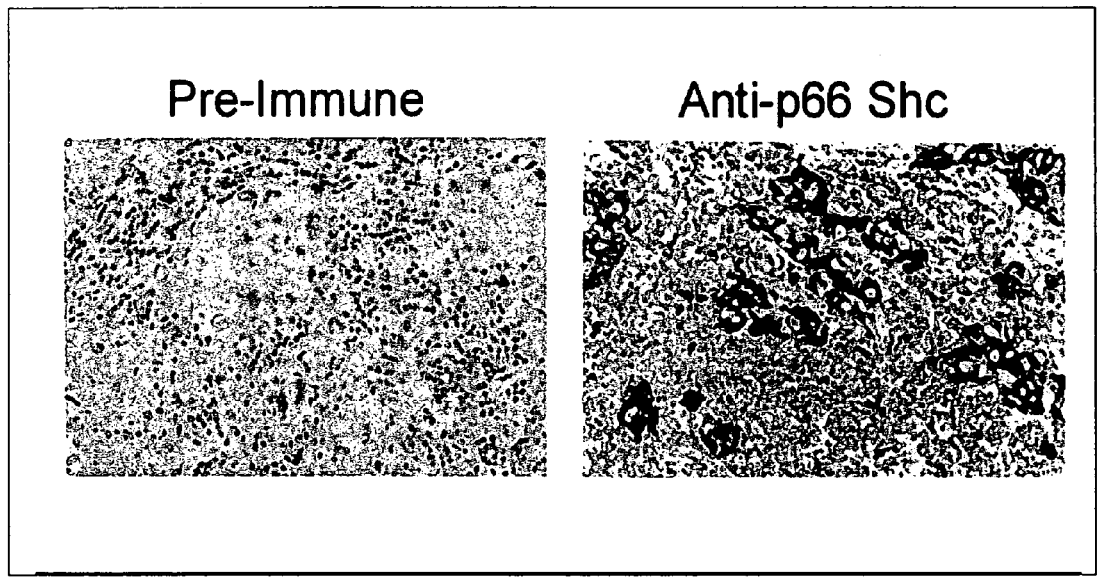
FIG. 6. Immunohistochemical specificity of the p66-isoform specific Rabbit polyclonal antibodies to She. Sections from a paraffin-embedded, formalin-fixed breast cancer specimen were stained with pre-immune immunoglobulin (Pre-Immune) or our rabbit antibody specific for p66 Shc (anti-p66 Shc).

The characterization of the #405 antibody was extended to immunohistochemical staining of archival, formalin-fixed, paraffin-embedded breast cancer specimens. A typical example (FIG. 6) reveals breast tumor cells intensely staining for p66 Shc, while the much more abundant lymphocytic infiltrating cells are completely lacking in staining. (It is well known that mature cells of hematopoetic lineages lack p66 Shc). Because of the large number of infiltrating lymphocytes, if this whole tumor had been extracted and immunoblotted for Shc, one would have concluded incorrectly that the tumor cells were deficient in p66 Shc, thus underscoring the importance of our approach of evaluating p66 Shc by immunohistochemical analysis. As it was seen for the PY-Shc staining, the pre-immune sera caused no non-specific background staining (FIG. 6, Pre-Immune). Details of the immunohistochemical evaluation of breast cancers for p66 Shc staining are provided below.

Monoclonal Antibodies Specific for p66Shc CH2 Domain

The expressed, purified and quality controlled Glutathione-S-transferase(Gst)-p66 Shc CH2 fusion protein (see above) was used to immunize 10 BALB/C mice (50 g in 40 l Titermax (Cytrex), adjuvant). After several boosts, two mice showed high titer antibodies that recognized the CH2 domain by ELISA, immunoprecipitated and immunoblotted p66 Shc specifically from breast cell detergent extracts, and recognized p66 Shc specifically in immunohistochemical analysis of breast cancers. After at least one month's rest, one of these mice was challenged on day −4 with 40 μg of soluble GST-CH2 (no adjuvant), and the other mouse was challenged on day −3 with an intravenous injection of 40 μg of soluble GST-CH2. Then on day 0, the mice were euthanized (by carbon dioxide inhalation), their spleens aseptically removed, spleen cells harvested and fused to the X8-653 myeloma fusing partner, using the Hybridoma Kit (StemCell Technologies), and following the manufacturer's instructions. On day 1, cells were seeded into 10, 100 mm tissue culture plates in methylcellulose-containing media containing the aminopteran selection agent. After 12 days, each plate contained nearly 400 individual clones.

Figure 7:
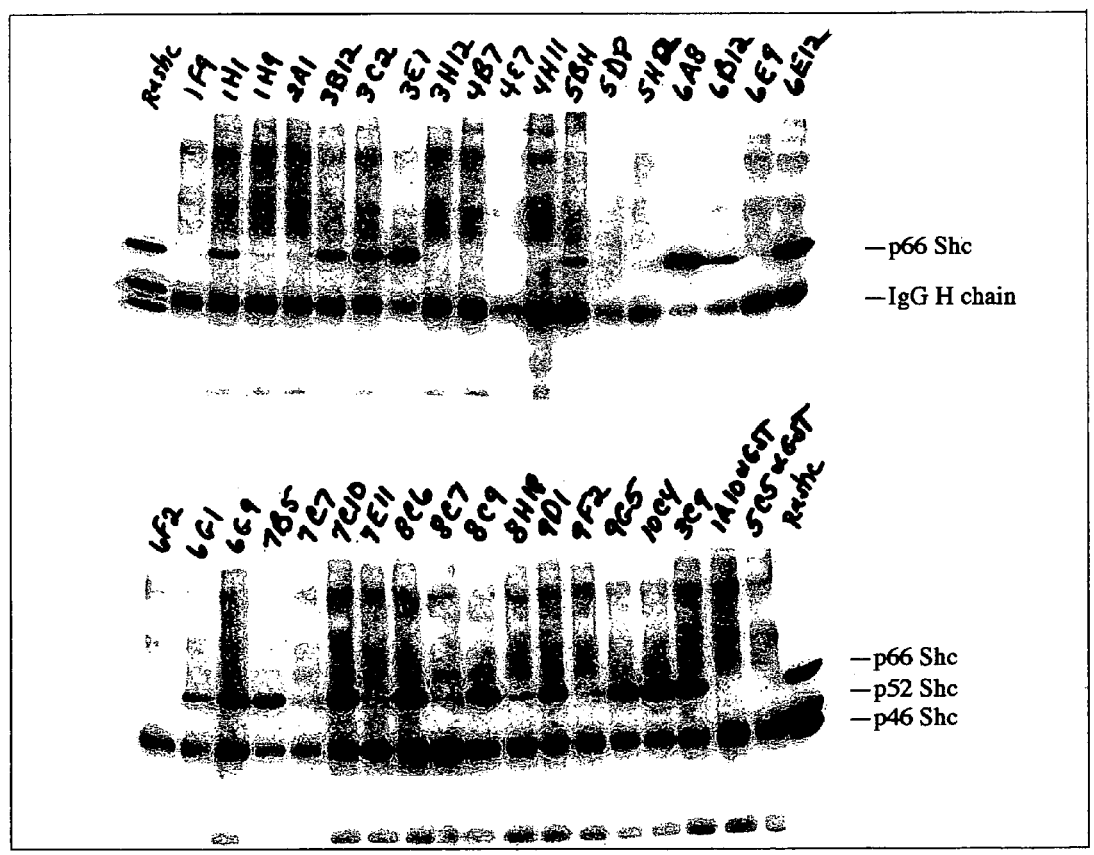
FIG. 7. Screening of monoclonal antibodies to 66-kDa Shc isoform for their ability to immunoprecipitate p66 Shc from cell extracts. Monoclonal antibodies from hybridoma culture supernatants were each reacted with 10 μl of an immunosorbant comprised of rabbit anti-mouse IgG (heavy and light chain specific) antibodies that had been covalently linked to cyanogen-bromide-activated Sepharose beads. These beads (and as a positive control, pan-Shc rabbit antibodies linked covalenty to Protein A-Sepharose 4B-CL beads, see lanes labeled "RαShc") were used to immunoprecipitate proteins from detergent extracts of MDA-MB-453 cells that we had engineered to express normal levels of human p66 Shc. The immunoprecipitates were resolved by SDS PAGE, immunoblotted with RαShc, and visualized by chemiluminescence. The positions of the 66-kDa, and in the positive controls, the 52- and 46-kDa Shc proteins are indicated. The RαShc immunosorbant, but not the hybridoma immunosorbants, were covalently crosslinked with dimethylpimelimedate, thus accounting for the IgG Heavy Chains non-specific staining and background bands in the hybridoma lanes. Note that two hybridomas that reacted by ELISA strongly against the GST-irrelevant protein (CH1) 1A 10αGST abd 5C5αGST) did not immunoprecipitate p66 Shc.

From 8 of the 10 plates, 960 clones were picked and transferred into 96-well liquid cultures. After 3-4 days of culture, supernatant culture fluids were tested by ELISA, comparing reactivity with recombinant GST-CH2 to reactivity with a GST-containing irrelevant fusion protein (GST-CH1). Supernatants of the 90 hybridomas with strongest reactivity to GST-CH2, but with little or no reactivity to the irrelevant GST-CH1, were tested further variously for their ability to specifically recognize p66 Shc by immunoblotting and by immunoprecipitation from clones of MDA-MB-453 cells (that had been engineered to express normal levels of p66 Shc). Six of the hybridoma antibodies specifically immunoblotted p66 Shc; at least 18 specifically immunoprecipitated Shc (see FIG. 8) Testing of 6 of these antibodies revealed that at least 4 (clones 6E12, 6G9, 7C10, and 8C6) recognized p66 Shc in immunohistochemical staining of breast cancer sections, with one antibody, 8C6, staining comparably to the polyclonal rabbit anti-p66 seen in FIG. 6. The 8C6 monoclonal antibody also is one of the most efficient at immunoprecipitating (FIG. 7) and immunoblotting p66 Shc, comparable to or better than the pan-Shc commercial available antibody. Isotyping revealed that all of the effective hybridomas were either IgG1 or IgG2a, with 6G9 and 8C6, among others, being IgG2a thus they bind very strongly to Protein A, a very useful property for purification and for their employment in various immunological assays/procedures. The monoclonal antibodies were purified from overgrown hybridoma culture supernatants by Protein A Sepharose 4B-affinity chromatography by standards methods well known to those skilled in the art.

Insofar as the other monoclonal antibodies recognize different epitopes on p66 Shc not recognized by 8C6, pooling of the antibodies will offer special advantages for immunohistochemical analysis, pooling such antibodies would provide additive signals and increase assay sensitivity. Further, in non-denatured cell extracts, some epitopes may be hidden by cellular proteins that bind to p66 Shc: thus for mechanistic studies, antibodies to other epitopes would allow one to immunoprecipitate the sub-populations of p66 Shc that are associated with such other proteins.

Rα Shc antibody, which recognizes all phosphorylated or unphosphorylated isoforms of Shc, and the 4G10 monoclonal antibody, which recognizes phosphotyrosine, were purchased from Upstate Biotechnology Inc. (Lake Placid, N.Y.).

Cells

HBL-100 cells (American Type Culture Collection [ATCC], Rockville, Md.) are a non-tumorigenic human breast-epithelial cell line that express a high level of EGF receptors. HBL-100/wt Shc 26 and HBL-100/dn Shc 17 were derived by G418 selective pressure after Lipofectamine-Plus transfection with pEBG vector carrying the cDNA (with expression driven by the constitutive EF1α promoter) for either wild-type $p52^{Shc}$-GST or a dominant-negative mutant $p52^{Shc}$Y317F-GST, respectively [for methodological details, see 42]. SKBR3 cells (ATCC) and MDA-MB-453 cells (ATCC) are transformed epithelial cell lines derived from human breast cancer that over express the ErbB2 member of the EGF-receptor family and therefore, have constitutively tyrosine-phosphorylated Shc. SKBR3 expresses a very small amount of p66 Shc, and normal amounts of p52 and p46 Shc; MDA-MB-453 does not express the $p66^{Shc}$ isoform. All of these cell lines were cultured in IMDM (Gibco) supplemented with 10% fetal bovine serum (Gibco), and pen/strep 1× antibiotics (Gibco) at 37° C. in 5% carbon dioxide, humidified atmosphere.

ELISA for Antibodies

Immunlon II microtiter wells were coated with PY-Shc or $p66^{Shc}$-CH2 peptide (1 μg/50 μll) in PBS, blocked with 1% BSA in PBS, and then incubated sequentially with the respective test rabbit antibodies or monoclonal antibodies, with a conjugate of horse-radish peroxidase linked to donkey antibody to rabbit immunoglobulin (or to rabbit anti mouse immunoglobulin, as appropriate), and finally with the chromogenic HRP substrate, o-phenylenediamine. ABS 450 nm was monitored.

Immunoprecipitation and Immunoblotting

Cells were either stimulated or not stimulated with EGF (100 ng/ml for 10 or 20 min), as indicated, and then extracted with 1% Triton X-100 in a buffer containing protease, kinase and phosphatase inhibitors [38]. Proteins were immunoprecipitated with either the new antibodies or commercial antibodies to Shc or PY. These antibodies were pre-bound to protein A-Sepharose 4B-beads (Sigma) and stabilized by cross-linking with dimethylpimelimidate (DMP) [38]. The immunoprecipitated proteins were resolved by SDS-PAGE, transferred to nitrocellulose membranes, and immunoblotted with the specified antibodies. Bound antibodies were then detected by enhanced chemiluminescence (ECL, Amersham).

Immunocytochemistry

Cells were seeded into chamber slides and incubated until reaching approximately 60-65% confluence. Cells were serum starved in phenol red-free medium before some chambers were stimulated with EGF (100 ng/ml for 20 min). Cells were rinsed with PBS and then fixed in 10% buffered-formalin for 10 min. Immunocytochemical staining was carried out according to the manufacturer using the Catalyzed Signal Amplification (CSA) Peroxidase System (DAKO, Carpinteria, Calif.) following Target Retrieval with the CSA Ancilliary System (DAKO). Primary antibodies: MaPtyr (5 μg/ml); RαShc (5 μg/ml); Rabbit #58-Pre-Immune (70 μg/ml or 7 μg/ml); Rabbit #58 (10 μg/ml or 1 μg/ml); Rabbit #405 p66-Pre-Immune (80 μg/ml or 8 μg/ml); and Rabbit #405 antibody to p66 (40 μg/ml or 4 μg/ml) were diluted in Background Reducing Components (CSA Ancillary System) and incubated with respective cell samples for 1 h at room temperature. Primary antibody was detected by incubating for 15-30 min with one of the following: biotinylated rabbit anti-mouse or goat anti-rabbit, or secondary antibody conjugated to HRP.

Tumor Tissues and the Patient Study Population

Archival, formalin-fixed, paraffin-embedded, unstained specimens were obtained from the Dept. of Pathology using information in the Roger Williams Cancer Center Tumor Registry, cross-checked with patient records. Tumors removed from 97 previously untreated patients diagnosed with breast cancer from 1990 to 1995 were utilized in a retrospective study. The study population had a median age of 63 yrs at diagnosis, and was comprised of 6 patients with AJC Stage 0 (DCIS), 39 with AJC Stage 1, 43 with AJC Stage 2, 5 with AJC Stage 3, and 4 with AJC Stage 4 disease, and had a mean follow-up time of 5.9 years, excluding those whose disease recurred before 5 years. In addition to surgery, patients subsequently received, variously, radiotherapy, hormone, taxol or chemotherapy. Of the 93 patients without metastatic disease, 64 were node negative for tumor cells. In total, 17 patients developed recurring disease, 15 of which were patients in AJC Stages <4.

Immunohistochemistry

Archival, formalin-fixed, paraffin-embedded breast tumor specimens identified through our Tumor Registry were retrieved, cut into 5 micron sections, mounted on slides, deparaffinized using xylene and ethanol, and stained with our polyclonal rabbit antibodies to PY-Shc or to p66 Shc (or monoclonal mouse antibodies to p66 Shc) using the Catalyzed Signal Amplification (CSA) Peroxidase System (DAKO, Carpinteria, Calif.) following Target Retrieval and endogenous peroxidase quenching with the CSA Ancillary System (DAKO), according to the kit's instructions. Primary antibodies: MaPtyr (5 μg/ml); RαShc (5 μg/ml); αR58-Pre-Immune (70 μg/ml or 7 μg/ml); αR58 (10 μg/ml or 1 μg/ml); αp66-Pre-Immune (80 μg/ml or 8 μg/ml); and αp66 (40 μg/ml or 4 μg/ml) were diluted in Background Reducing Components (CSA Ancillary System) and incubated with respective cell samples for 1 h at room temperature. Primary antibody was detected by incubating for 15-30 min with one of the following: biotinylated rabbit anti-mouse or goat anti-rabbit, or secondary antibody conjugated to HRP. The antigen-antibody signal was detected by diaminobenzidine (DAB) precipitation at the antigen site.

The immuno-histochemical grading system involves estimating the staining intensity (Intensity =I, 0-5 scale) of the tumorous glandular tissue, and the total fraction of glandular tissue that stains at each of the 6 possible intensities (Distribution=D, 0-10 scale, where 10=100% of the tumor tissue, 5=50%, etc). To arrive at an average staining intensity for the entire tumor slice, the sum of the products of the staining intensities and their respective distributions is taken, and then the result is scaled to arrive at a final index (DI) that could range from 0 to 1. The formula, then, is:

$$DI = \{[(\text{intensity score} + \text{distribution score}/2)]/\times\}/10,$$
where: intensity score=1 thru 5

(0=negative, background staining only)
1=low level, punctate and non-uniform staining pattern
2=low level punctate and uniform staining pattern
3=low level, evenly distributed cellular staining pattern
4=moderate levels evenly distributed cellular staining pattern 5=high level, evenly distributed cellular staining pattern distribution score ductal region staining positive (with 10=100%; 5=50%, etc.).

x=the number of regions with different intensity scores (for example: [(5+2/2)+(4+5/2)+(2+3/2)/3]/10=0.53, this means that 20% of the biopsy stained with an intensity of 5, 50% stained with intensity of 4, and 30% stained with intensity of 2.)

Although both PY-Shc and p66 Shc staining indices can be used as independent markers (see data, below), it was expected, from the analysis of their biochemical functions discussed, above, that the relative staining levels of PY-Shc to p66 Shc in any particular tumor (or even better, in any one cell, because tumors are heterogeneous) would provide a much more useful indicator of a tumor's potential aggressiveness. Accordingly, this was addressed by computing the Ratio of the indices for PY-Shc to p66 Shc.

Figure 9:
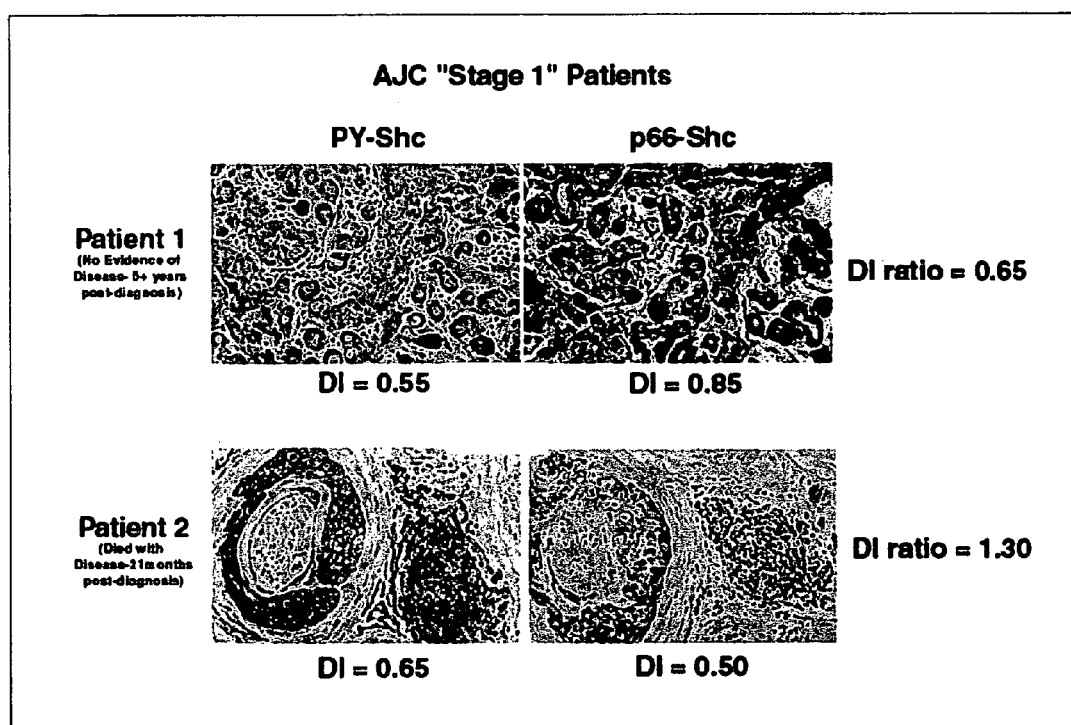
FIG. 9. Examples of the scoring system for the immunohistochemical staining of breast cancers. Breast cancer specimens were reacted with rabbit antibodies specific for PY-Shc or for p66-Shc and stained as in FIG. 8 using the CSA kit from DAKO, with hematoxylin counterstaining.

Examples of the scoring system for the entire range of staining intensity are shown in FIG. 8 using prostatic cancer specimens and PY-Shc staining. Specific, comparative PY-Shc and p66-Shc staining in two patients with breast cancer are shown in FIG. 9.

Prognostic Utility of Shc Markers Early Stage and Nondenegative Breast Cancer

Preliminary Analysis of a Study Population Comprised of Patients Presenting with AJC Stages 0 through 4 Breast Cancer Analysis of PY-Shc and p66 staining indices for the 97 patients in our Study Population (17 of whom developed recurring disease) revealed considerable variability, but with apparent differences between values for patients whose disease recurred and those whose disease did not recur, especially for the Ratio index (Table 1).

TABLE 1

Summary Statistics for PY-Shc and p66-Shc Staining

| Marker | Mean | Range | S.D. |
|---|---|---|---|
| All Patients (97) in Study | | | |
| PY-Shc | 0.33 | 0-0.84 | 0.20 |
| p66 Shc | 0.58 | 0.10-0.93 | 0.21 |
| PY-Shc/p66-Shc Ratio | 0.68 | 0-3.56 | 0.60 |
| Patients who remained disease free for at least 5 years (52) | | | |
| PY-Shc | 0.30 | 0-0.74 | 0.18 |
| p66 Sho | 0.59 | 0.1-0.93 | 0.20 |
| PY-Shc/p66-Shc Ratio | 0.62 | 0-3.56 | 0.59 |
| Patients who developed recurrent disease (15) | | | |
| PY-Shc | 0.45 | 0.08-0.84 | 0.22 |
| p66 Shc | 0.55 | 0.24-0.92 | 0.22 |
| PY-Shc/p66-Shc Ratio | 0.98 | 0.09-2.17 | 0.59 |

Figure 10:
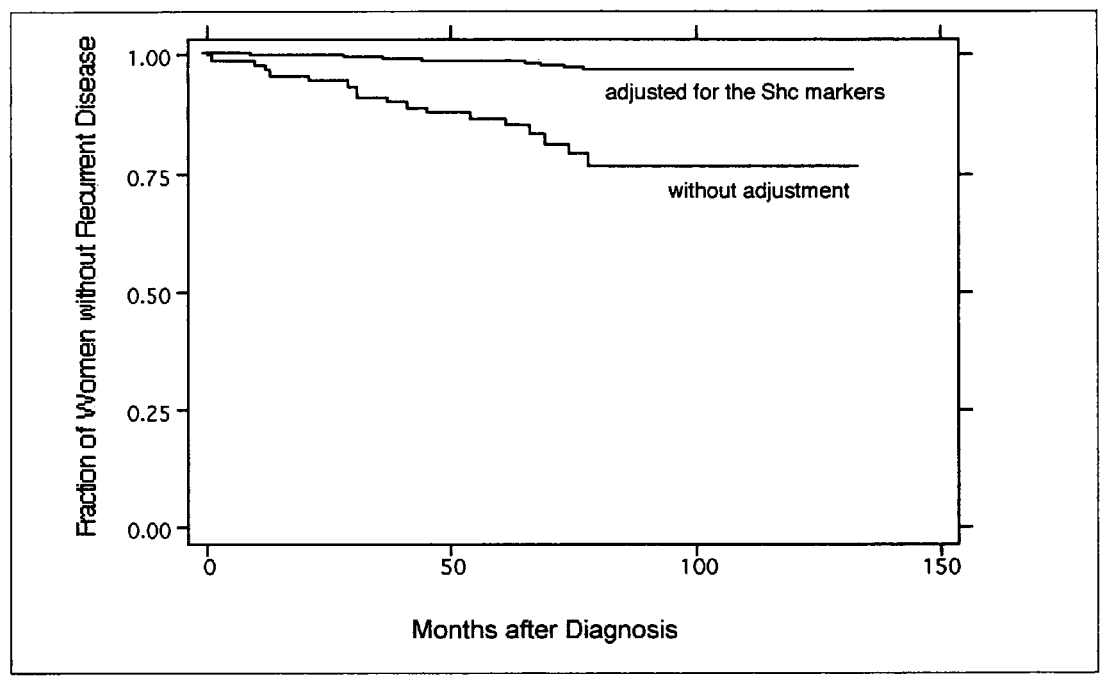
FIG. 10. Kaplan-Meier Plot showing "time-to-failure" (or disease recurrence) in the total study population of 97 women with breast cancer. By adjusting the plot for zeroing values of the PY-Shc and p66-Shc markers, these markers appear to account for most of disease recurrence in women initially diagnosed with AJC Stages 0-4 of breast cancer FIG. 11. Kaplan-Meier Plot showing "time-to failure" (or disease recurrence) in the total study population of 97 women with breast cancer. Top panel: By dichotomizing the Py-Shc scores into Low (<0.33) and (>=0.33), the risk of recurring disease is clearly increased in patients with High levels of PY-Shc, and decreased in patients with low tumor levels of PY-Shc. Bottom Panel: Similarly by dichotomizing the Shc Ration indices into Low (<0.65) and High (>=0.65), the risk of recurring disease is clearly is clearly increased in patients with High levels of PY-Shc, and decrease in patients with low tumor levels of PY-Shc.

Kaplan-Meier (K-M) "Survival" curves ("Disease Recurrence" curves, all statistical analysis were performed using the "Intercooler Stata" statistical software, Stata Corporation, College Station, Tex.) showed an overall 26% recurrence at 5 years follow-up (FIG. 10). Cox Proportional Hazards analysis showed excellent model fits, with PY-Shc index having a Hazards Ratio of 27 with a highly significant P>Izl of 0.005, the p66-Shc, having a trend (but not yet—significant P value) towards a negative (<1) Hazards Ratio of 0.34 (much as predicted from the biology of the Shc proteins). The Shc Ratio index had a positive Hazards Ratio of 1.89, with a very significant P value of 0.016. Indeed, mathematically adjusting the Kaplan-Meier curves for zeroing values of PY-Shc and p66 Shc virtually eliminated the theoretical risk of tumor recurrences (from 26% down to 3.6%, see FIG. 10).

Figure 11:
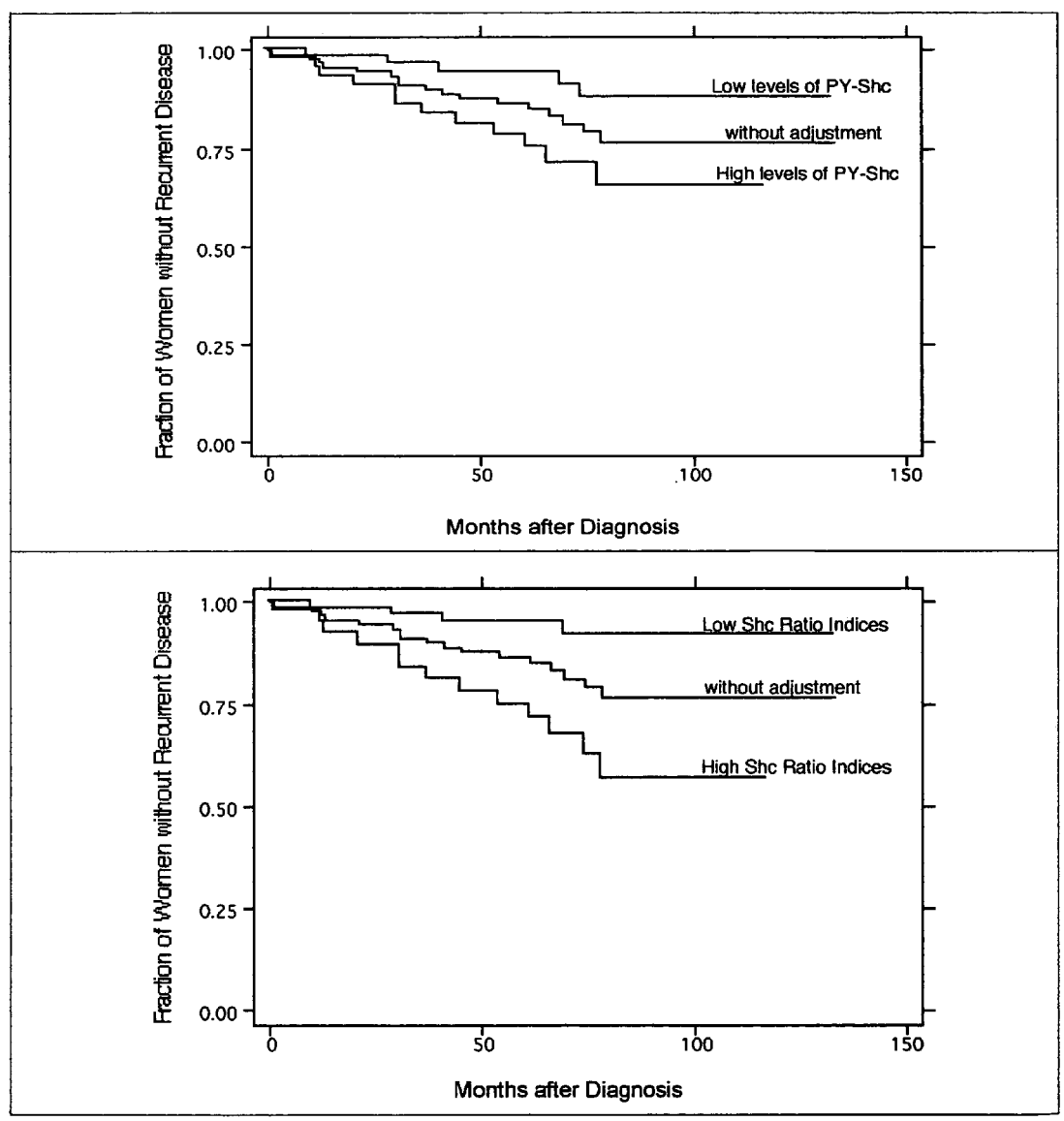

Dichotomizing the PY-Shc values into Low (<0.33) or High (>=0.33) and the Shc Ratio Index into Low (<0.65) and High (>=0.65) resulted in dramatically different K-M plots (FIG. 11). Log Rank test comparisons of the dichotomized PY-Shc "Survival" curves revealed that the High PY-Shc patients indeed had a very significantly higher rate of disease recurrence than the Low PY-Shc population (P>$X^2$ of 0.01). A similar conclusion was reached for the High Ratio patients (P>$X^2$ of 0.005). The Low PY-Shc and the Low Ratio patients had a very low rate of recurrent disease (9% and 7%, respectively, see Table 2) compared to the High PY-Shc (28%) and the High Ratio (34%) patients.

TABLE 2

The Ability of the Shc Ratio Index to Identify Patients of All AJC Stages who are Destined to Develop Recurrent Disease

| | Recurrent Disease? | | |
|---|---|---|---|
| | No | Yes | Total Patients |
| PY-Shc Index | | | |
| Low | 49(91%) | 5(9%) | 54(56%) |
| High | 31(72%) | 12(28%) | 43(44%) |
| Totals | 80(82%) | 17(18%) | 97(100%) |
| Shc Ratio Index | | | |
| Low | 55(93%) | 4(7%) | 59(61%) |
| High | 25(66%) | 13(34%) | 38(39%) |
| Totals | 80(82%) | 17(18%) | 97(100%) |

Pearson $\chi^2$ = 5.8, Probability = 0.016

Pearson $\chi^2$ = 12.0, Probability < 0.001

Patients with Early, AJC Stage 0 and Stage 1 Disease

Figure 12:
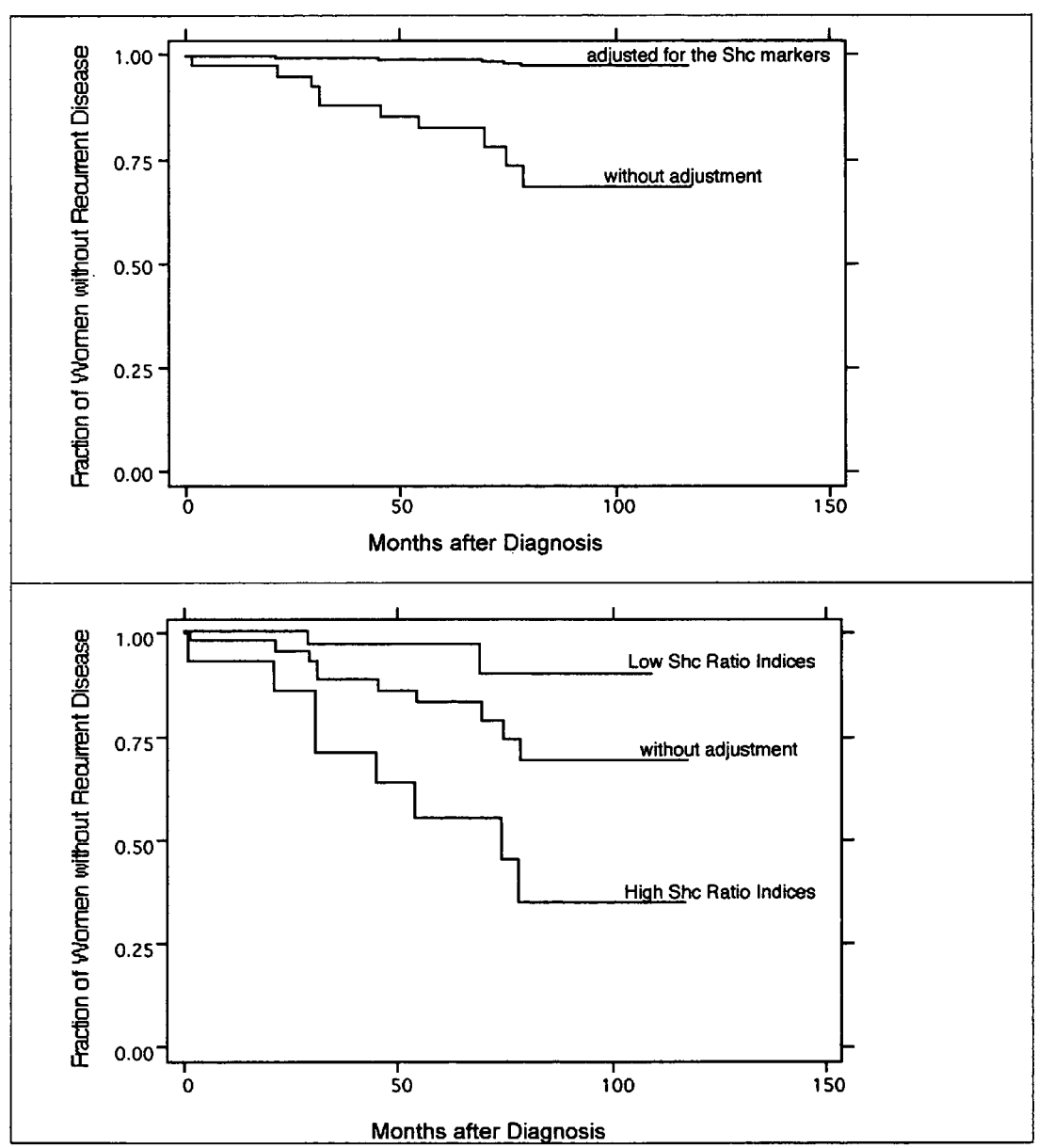
FIG. 12. Kaplan-Meier Plot showing "time-to-failure" (or disease recurrence) in women with early, AJC Stage O, and Stage 1 breast cancer. Top panel: By adjusting for zeroing values of the PY-Shc and p66-Shc markers, these markers also appear to account for most of the risk of disease recurrence in patients diagnosed with early Stage breast cancer. Bottom panel: By dichotomizing the Shc Ratio indices into Low (<0.65) and High (>=0.65), the risk of recurring disease is clearly increased in patients with High levels of PY-Shc, and decrease in patients with low tumor levels of PY-Shc.

More than 100,000 women are expected to be diagnosed with early stage breast cancers (Stage 0 or Stage 1) in the year 2002. Because there are no reliable prognostic markers for this large and clinically problematic group of women, the prognostic value of the Shc markers in the subpopulation of AJC Stage 0 and 1 cancers (45 subjects with 10 instances of recurrent disease) was determined. Adjusting the K-M plots of Stage 0, 1 patients for zeroing values of PY-Shc and p66 Shc again greatly reduced the theoretical risk of tumor recurrence (from 37% to 2.3%, see FIG. 12). Cox Proportional Hazards analysis showed excellent model fits and P values for PY-Shc and p66 Shc and an extremely significant Shc Ratio index {5.0 (P>0.001) see Table 3}. The Hazard ratios were much greater than 1.0 for PY-Shc and for the Shc Ratio Index, indicating that increasing values of PY-Shc and the Shc Ratio Index are associated with greatly increasing risk of disease recurrence. Conversely, the Hazard ratio was much less than 1.0 for p66-Shc, indicating that decreasing values of p66-Shc are associated with greatly increasing risk of disease recurrence.

TABLE 3

Cox Proportional Hazards Analysis for the Risk of Recurrent Disease in Patients Diagnosed with AJC Stages 0 and 1 Disease, as a Function of Elevated PY-Shc and Decreased p66-Shc Levels

| Marker | Haz. Ratio | Std. Err. | z | P > |z| | 95% Conf. Interval |
|---|---|---|---|---|---|
| PY-Shc | 50.8 | 83 | 2.39 | 0.017 | 2.0-1300 |
| p66-Shc | 0.033 | 0.050 | -2.27 | 0.023 | 0.0018-0.62 |
| Shc Ratio | 5.0 | 2.4 | 3.39 | 0.001 | 2.0-13 |

LR $\chi^2$ = 8.81 Log likelihood = -29.6 Prob > $\chi^2$ = 0.0122
LR $\chi^2$ = 9.15 Log likelihood = -29.4 Prob > $\chi^2$ = 0.0025

Again, even for these early AJC Stage patients for whom no good prognostic indicator has been available, the rate of recurrent disease was very low in patients who had Low Shc Ratios (6% recurrence) compared to the total population (22% recurrence), while the patients with High Shc Ratios had a very high rate of recurrent disease (62% recurrence) compared to the total population (22%, see Table 4). Log Rank test comparisons of "Survival" curves dichotomized into groups of Low and High Shc Ratios (FIG. 12) revealed that the heightened risk of recurrent disease for patients with High Shc Ratios compared to the patients with Low Shc Ratios (62% vs. 6%) was extraordinarily significant (P>Chi$^2$ of 0.0007).

TABLE 4

The Ability of the Shc Ratio Index to Identify AJC Stage 0 & 1 Patients Destined to Develop Recurrent Disease

| Shc Ratio Index | | Recurrent Disease? | | Total Patients |
|---|---|---|---|---|
| | | No | Yes | |
| Low | Patients | 30 | 2 | 32 |
| | Row | 94% | 6% | 100% |
| | Column | 86% | 20% | 71% |
| | Cell | 67% | 4% | 71% |
| High | Patients | 5 | 8 | 13 |
| | Row | 38% | 62% | 100% |
| | Column | 14% | 80% | 29% |
| | Cell | 11% | 18% | 29% |
| Totals | Patients | 35 | 10 | 45 |
| | Row | 78% | 22% | 100% |
| | Column | 100% | 100% | 100% |
| | Cell | 78% | 22% | 100% |

Pearson $\chi^2$ = 16.3, Probability << 0.001

Patients with Node Negative Breast Cancer

Figure 13:
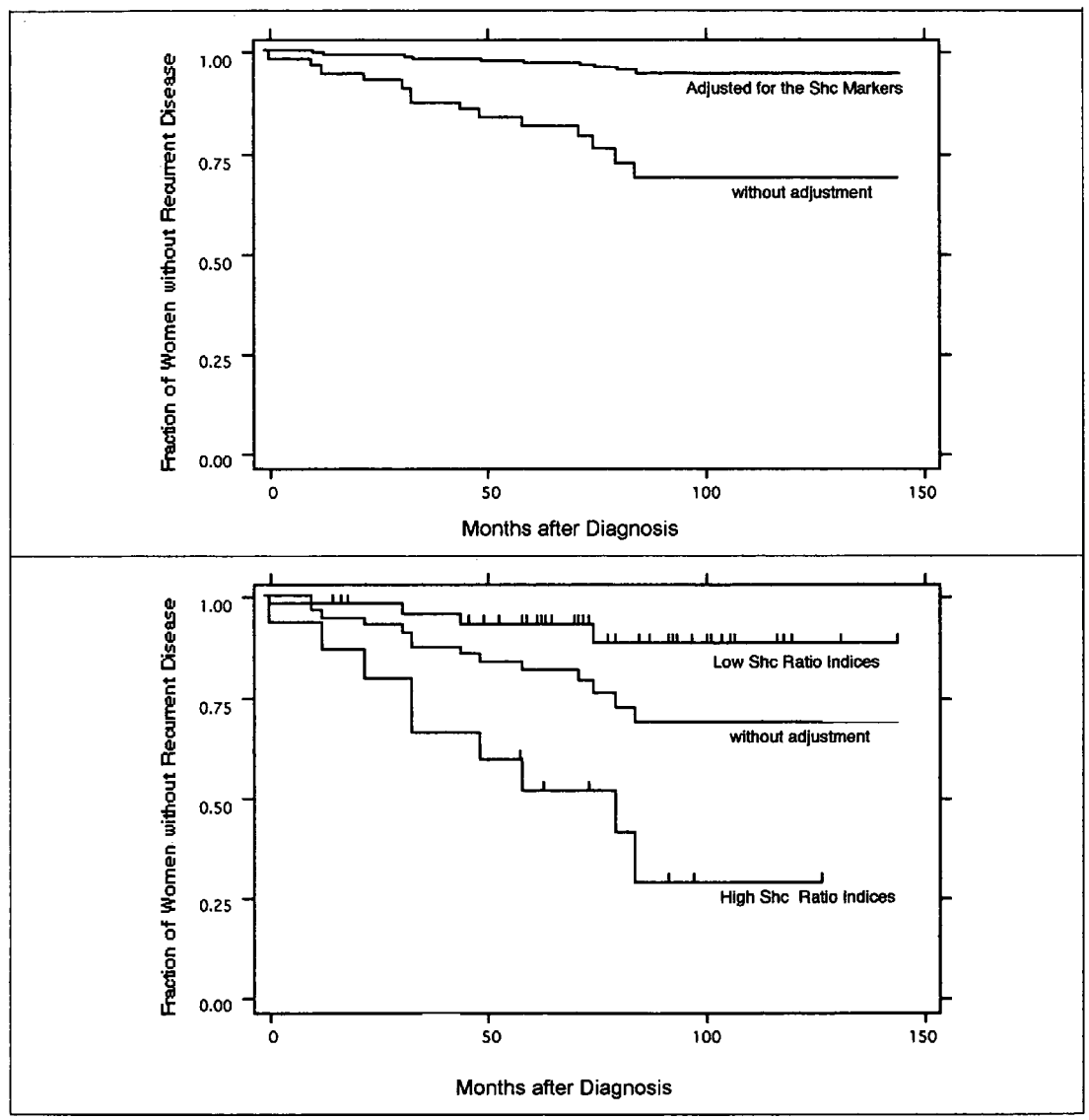
FIG. 13. Kaplan-Meier Plot showing "time-to-failure" (or disease recurrence) in women with lymph-node negative breast cancer. Top panel: By adjusting for zeroing values of the PY-Shc and p66-Shc markers, these markers also appear to account for most of the risk of disease recurrence in patients diagnosed with node negative breast cancer. Bottom panel: by dichotomizing the Shc Ratio indices into Low (<0.65) and High (>=0.65), the risk of recurring disease is clearly increased in patients with High levels of PY-Shc, and decrease in patients with low tumor levels of PY-Shc.

An even larger proportion of breast cancer patients (comprised of all Stage 0, 1, many Stage 2 and a few Stage 3 patients) present with disease that has not detectably spread to regional lymph nodes (node negative patients). Although these patients can be subdivided based on estrogen-receptor status, tumor size and histological grade into a relatively Low Risk group and High Risk group [1], the different risk-group classifications provide still a very poorly-performing prognostic tool. Therefore, the PY-Shc and p66-Shc levels in this subset of patients (61 patients, 13 of whom developed recurring disease) was analyzed. Adjusting the K-M plots of these node-negative patients for zeroing values of PY-Shc and p66 Shc greatly reduced the theoretical rate of tumor recurrence, from 30% down to 4.6% (FIG. 13), suggesting that most of the tumor recurrence could be accounted for by heightened PY-Shc and lowered p66-Shc levels. Cox Proportional Hazards analysis of the Shc Ratio indices showed excellent model fits (Chi$^2$=6.2, Probability>Chi$^2$ of 0.013) and an extremely significant (P>0.005) Hazards Ratio (3.2)(see Table 5).

TABLE 5

Cox Proportional Hazards Analysis for the Risk of Recurrent Disease in Patients Diagnosed with Node Negative Disease, as a Function of Elevated PY-Shc and Decreased p66-Shc Levels

| Marker | Haz. Ratio | Std. Err. | z | P > |z| | 95% Conf. Interval |
|---|---|---|---|---|---|
| Shc Ratio | 3.3 | 1.4 | 2.81 | 0.005 | 1.4-7.6 |

LR $\chi^2$ = 6.22 Log likelihood = -46.8 Prob > $\chi^2$ = 0.013

Once again, even for these node-negative patients for whom no good prognostic indicator has been available, the Low Shc Ratio patients had a very low rate of recurrent disease (8.5% recurrence) compared to the total population (21% recurrence), while the High Shc Ratio patients had a very high rate of recurrent disease (56% recurrence) compared to the total population.

TABLE 6

The Ability of the Shc Ratio Index to Identify Node Negative Patients Destined to Develop Recurrent Disease

| Shc Ratio Index | | Recurrent Disease? | | Total Patients |
|---|---|---|---|---|
| | | No | Yes | |
| Low | Patients | 43 | 4 | 47 |
| | Row | 92% | 8.5% | 100% |
| | Column | 86% | 31% | 75% |
| | Cell | 68% | 6% | 75% |
| High | Patients | 7 | 9 | 16 |
| | Row | 44% | 56% | 100% |
| | Column | 14% | 80% | 29% |
| | Cell | 11% | 18% | 29% |
| Totals | Patients | 50 | 13 | 63 |
| | Row | 79% | 21% | 100% |
| | Column | 100% | 100% | 100% |
| | Cell | 79% | 21% | 100% |

Pearson $\chi^2$ = 16.6, Probability << 0.001

Log Rank test comparisons of the dichotomized Shc Ratio "Survival" curves (FIG. 13) revealed an extraordinarily significant, higher rate of disease recurrence among patients with High Shc Ratios (56%, 9/16 patients) than among patients with Low PY-Shc Ratios (8.5%, 4/49 patients, $X^2$=16.3, Probability>$X^2$ of <<0.001).

Categorizing our node-negative patients into the recently defined "Consensus Low Risk" and "Consensus High Risk" groups, the ability of the Consensus Risk classification and the dichotomized Low and High Shc Ratio classifications to correctly predict tumor recurrence and to incorrectly fail to predict tumor recurrence was compared. As can be seen in FIG. 14, the Consensus classification was unable to predict which patients would and which patients would not suffer from recurrent disease. In contrast, the Shc Ratio index accurately classified patients into Low and High risk groups. Patients in the Low Shc Ratio group had only a 13% incidence of recurring disease, while those in the High Shc Ratio group had a 60% incidence of recurring disease. In contrast, the Consensus Panel's classification performed very poorly: in its "Low Risk" group, although small in number, 3 out of its 7 patients had recurring disease (43%), while in its "High Risk" group, 10 out of its 39 patients (26%) had recurring disease.

In summary, the use of the Shc markers, either the PY-Shc or the p66 Shc measurements alone, but preferably used together as a Ratio offer a heretofore unattainable ability to categorize breast cancer patients into those with a very high likelihood of having recurrent disease and into those with a very low likelihood of having recurrent disease. The clinical impact and the improvement—in the quality of life for hundreds of thousands of women each could be enormous. For many women who are currently recommended to undergo intensive adjuvant therapy could be spared that morbidity and expense, while others who suffer recurrent disease because they are currently inappropriately not recommended for intensive adjuvant therapy would now, based on the levels of their Shc markers, be recommended for intensive adjuvant therapy.

The likely usefulness of the Shc markers clearly extends beyond the detailed documented usefulness in breast cancer likely to prostate cancer and to many other cancers as well. Preliminary surveys of the Shc markers in prostatic cancer demonstrate, as we would predict, considerable variability in intensity and discordance with other markers that themselves merely correlate with the stage of the disease.

Example 2

Breast cancer remains the most common cancer diagnosed in women, with approximately 200,000 new cases each year in the United States alone [1]. The initial development of breast cancer, as well as its degree of aggressiveness, are in part controlled by signaling from diverse growth factors and their receptors (e.g. HER-2/neu, other EGF receptor family members, and IGF-1), from integrins, and from G-protein-coupled receptors [2-6]. Virtually all of these signals involve one or more tyrosine kinases.

Currently the National Cancer Institute lists more than 95 open or planned clinical trials employing a myriad of tyrosine kinase inhibitors (TKI) specific for Her-2/neu, the EGF receptor or any of several other receptor and non-receptor tyrosine kinases. However, these trials in general are greatly hampered by the clinician's inability to predict which patients have tumors that are likely to respond to any single or combination of TKIs.

Because Shc tyrosine phosphorylation is intimately involved in the malignant phenotype and serves as a reporter of aggressive tumors, we expect that the Py-Shc can be used as an in vitro predictor of anti-tumor effectiveness of TKIs. Such an assay could have a major impact upon both the development (phase 2 and 3 clinical testing) and ultimate use of tyrosine kinase inhibitors to treat breast cancer. The clinician could streamline this adjuvant therapy for breast cancer patients, and administer it only to patients whose tumors are likely to be responsive to it. It is likely that this assay would be similarly useful in prostate, ovarian, and other cancers.

Materials and Methods

It has been shown previously that Shc tyrosine phosphorylation is human breast cancer cell lines can be inhibited by brief (<2 hr) exposure in tissue culture to effective TKIs [54, 16]. For human breast tumors, such an assay would involve coring a piece of an excised primary tumor with an 18 g needle and slicing the cores into 0.5 mm discs. Discs would be rinsed with Hank's solution and placed into wells of a 96-well tissue culture plate, with each well containing one or more TKI in 100 µl Hanks for about 2 hrs at 37° C. in a 5% $CO_2$ chamber. The tissue discs would then be recovered, fixed, paraffin-embedded and processed for quantitative immuno-histochemical staining of PY-Shc. It is expected that the ability of TKIs to reduce levels of tumor PY-Shc will correlate with the tumor's sensitivity to these TKIs.

Example 3

Additional Embodiments of the Invention

Immunological Based Assays (a) Immunohistochemical assays in which PY-Shc and p66 Shc are detected simultaneously using a two-color staining system.

(b) Immunohistochemical assays in which PY-Shc and p66 Shc are detected either separately or simultaneously using immunofluorescent tags and fluorescence microscopy.

(c) Immunoblotting of PY-Shc and of p66 Shc that has been extracted from tumor cells. This method is much less desirable in priniciple and in practice insofar as contaminating host stromal cells, non-cancerous glandular tissue and immune-cell infiltrates could grossly distort the estimate of PY-Shc and p66 Shc in the tumor. For example, lymphocytic infiltrate cells lack p66 Shc, and a tumor such as that depicted in FIG. 6 would, by immunoblotting, appear to be very deficient in p66 Shc, while in fact, the tumor cells themselves are rich in p66 Shc.

(d) ELISA based assays, Sandwich and competition types. Sandwich ELISA can use pan-anti-Shc as capture antibodies for tumor extracts, and then the PY-Shc-specific and the p66 Shc-specific antibodies for detection. Or, the antibodies can be used in reverse order.

(e) Flow-cytometric assays in which the tumor cells would be separated from one another and stroma using conventional enzymatic procedures known to those skilled in the art (e.g. dispase, collagenase treatment, etc), followed optionally by separation of tumor cells from stromal cells (density centrifugation, for example), fixing and permeablizing the cells (using standard procedures such as 70% ethanol), and then staining either singly or doubly for PY-Shc and p66-Shc using fluorescently tagged primary or secondary antibodies (or biotin/Avidin systems, or the like), and optionally adding a third antibody (tagged directly or indirectly with a third fluorophore) that is specific for breast (cancer) cells, such as MUC-1. One, two or three color flow cytometric analysis could then quantitate, on each individual cell, the PY-Shc and p66-Shc levels.

(f) A further embodiment is an immunoassay using a PY-Shc antibody directed to the Y239 and/or Y240 minor tyrosine phosphorylation sites on Shc, rather than, or in addition to, antibodies directed the Y317 tyrosine phosphorylation site.

(g) Immunoassays similar to those described in "c", above, but combining immunoprecipitation with pan-Shc antibodies and subsequent immunoblotting with pan-specific antibodies to phosphotyrosine such as the aforementioned 4G10 monoclonal antibody.

Non-Immunological-Based Assays for PY-Shc and p66 Shc (a) Modern methods have recently evolved that are capable of quantitating the amount of an individual protein, and even the amount of that protein that is post-translationally modified in a particular amino acid. One such procedure that has been described recently is single cell matrix-assisted laser desorption/ionization time-of-flight mass spectrometry (Maldi-TOF) [52, 53]. Single cell MALDI TOF could simultaneously determine the amounts of PY-Shc (either P[317]Y-Shc, P[239,240]Y-Shc, or both) and p66 Shc in individual tumor cells or in groups of tumor cells.

(b) Blotting assay similar to those described in "c" and "g", above, but using a ligand specific for the PY-Shc such as, but not limited to, the SH2 domain of the adaptor protein, Grb2. In this assay, Shc would be immunoprecipitated from tumor cell extracts using a pan-Shc antibody, and then probed by ligand (Grb2-SH2 domain). The amount of ligand bound to PY-Shc could be localized on the blot and quantitated by using a reagent that would react with the Grb2-SH2 domain. This reagent could be an HRP-tagged antibody to the Grb2-SH2 domain, a similarly tagged antibody directed to an artificial epitope (such as GST, FLG, HIS, or biotin) that has been fused to or coupled to the Grb2-SH2 domain. Alternatively, the Grb2-SH2 domain could be linked directly to a reporter enzyme, such as HRP (horse-radish peroxidase) or alkaline phosphatase.

Combinations of Assays for PY-Shc and p66 Shc and Other Mutant, Amplified or Activated Cellular Genes/Proteins Neoplastic transformation by certain oncogenes/oncogenic proteins are believed to not require activation of the PY-Shc signaling pathway at least to Ras/MAP kinase. Such alterations would include mutation of the RAS gene to produce Ras protein that is constitutively active. Although this occurs relatively rarely in breast cancer, such a mutation or otherwise non-Shc-dependent activation of Ras (e.g. by activated protein kinase C) could account for some of the aggressive breast cancers that seem not to be detected by the PY-Shc and p66 Shc markers. Similarly, over-expression or activation of c-Myc could drive cellular proliferation independently of the Shc pathways, and thus aberrancies in Myc levels/activity could also account for some of the aggressive breast cancers that seem not to be detected by the Shc markers. Thus, adding immunohistochemical or in-situ PCR-based detection of aberrant Ras and Myc levels/activities to the assay for the Shc markers would be expected to improve further the accuracy with which patients are assigned to the High Risk group for recurrent disease.

TABLE 7

The Shc Ratio Indices are much more effective than the current Consensus Clinical Guidelines in assigning risk of disease recurrence

| Node Negative Patients | Low Risk Shc Ratio (<0.65) | High Risk Shc Ratio (≧0.65) | Rate of Recurrence |
|---|---|---|---|
| Low Clinical Risk | Patients Recurring = 1 Non-Recurring = 3 Total = 4 | Patients Recurring = 2 Non-Recurring = 1 Total = 3 | 43% |
| High Clinical Risk | Patients Recurring = 3 Non-Recurring = 24 Total = 27 | Patients Recurring = 7 Non-Recurring = 5 Total = 12 | 26% |
| Rate of Recurrence | 13% | 60% | |

New Definition of Risk Categories for Patients with Node-Negative Breast Cancer

| Risk Category | Endocrine-Responsive | Endocrine-Nonresponsive |
|---|---|---|
| Low Risk | ER+ and/or PgR+, and all the following features: pT ≦ 2 cm, and Grade 1, and Age ≧ 35 years | Not Applicable |
| High Risk | ER+ and/or PgR+, and at least one of the following features: pT > 2 cm, or Grade 2-3, or Age <35 years | ER negative and PgR negative |

From Goldhirsch et at., Meeting Highlights: International Consensus Panel on the Treatment of Primary Breast Cancer. J Clin Oncol 19:3817-3827, 2001.

REFERENCES

1. Goldhirsch, A., et al., Meeting highlights: International Consensus Panel on the Treatment of Primary Breast Cancer. Seventh International Conference on Adjuvant Therapy of Primary Breast Cancer. J Clin Oncol, 2001. 19(18): p. 3817-27.
2. McGuire, W., et al., How to use prognostic factors in axillary node-negative breast cancer patients. J Natl Cancer Inst, 1990. 82: p. 1006-1012.
3. Berger, M. S., Locher, G. W., Saurer, S et al., Correlation of c-erbB-2 gene amplification and protein expression in human breast carcinoma with nodal status and nuclear grading. Cancer Research, 1988. 48: p. 1238-1243.
4. Hynes, N., Amplification and overexpression of the erbB-2 gene in human tumors: its involvement in tumor development, significance as a prognostic factor, and potential as a target for cancer therapy. Seminars in Cancer Biology, 1993. 4: p. 19-26.
5. Slamon, D. J., et al., Human breast cancer: correlation of relapse and survival with amplification of the HER-2/neu oncogene. Science, 1987. 235: p. 177-182.
6. Dickson, R. B. and M. E. Lippman, Growth factors in breast cancer. Endocr Rev, 1995. 16(5): p. 559-89.
7. Tuck, A. B., et al., Coexpression of hepatocyte growth factor and receptor (Met) in human breast carcinoma. Am J Pathol, 1996. 148(1): p. 225-32.
8. Nolan, M. K., et al., Differential roles of IRS-1 and SHC signaling pathways in breast cancer cells. Int J Cancer, 1997. 72(5): p. 828-34.
9. Mitchell, P. J., et al., Cloning and characterisation of cDNAs encoding a novel non-receptor tyrosine kinase, brk, expressed in human breast tumours. Oncogene, 1994. 9(8): p. 2383-90.
10. Luttrell, D. K., et al., Involvement of pp60c-src with two major signaling pathways in human breast cancer. Proc Natl Acad Sci USA, 1994. 91(1): p. 83-7.
11. Schechter, A. L., et al., The neu oncogene: an erb-B-related gene encoding a 185,000-Mr tumour antigen. Nature, 1984. 312(5994): p. 513-6.
12. Carraway, K. L. and L. C. Cantley, A neu acquaintance for erbB3 and erbB4: a role for receptor heterodimerization in growth signaling. Cell, 1994. 78(1): p. 5-8.
13. Hudziak, R., J. Schlessinger, and A. Ullrich, Increased expression of the putative growth factor receptor pl85HER2 causes transformation and tumorigenesis of NIH3T3 cells. Proc Natl Acad Sci, 1987. 84: p. 7159-7163.
14. Ben-Levy, R., et al., A single autophosphorylation site confers oncogenicity to the Neu/ErbB-2 receptor and enables coupling to the MAP kinase pathway. Embo J, 1994. 13(14): p. 3302-11.
15. Dougall, W. C., et al., The neu-oncogene: signal transduction pathways, transformation mechanisms and evolving therapies. Oncogene, 1994. 9(8): p. 2109-23.
16. Culouscou, J. M., et al., Characterization of a breast cancer cell differentiation factor that specifically activates the HER4/pl80erbB4 receptor. J Biol Chem, 1993. 268 (25): p. 18407-10.
17. Carraway, K. L. r., et al., Heregulin stimulates mitogenesis and phosphatidylinositol 3-kinase in mouse fibroblasts transfected with erbB2/neu and erbB3. J Biol Chem, 1995. 270(13): p. 7111-6.
18. Normanno, N., et al., Amphiregulin as an autocrine growth factor for c-Ha-ras- and c-erbB-2-transformed human mammary epithelial cells. Proc Natl Acad Sci USA, 1994. 91(7): p. 2790-4.
19. Cohen, G. B., R. Ren, and D. Baltimore, Modular binding domains in signal transduction proteins. Cell, 1995. 80(2): p. 237-48.
20. Pawson, T., Protein modules and signalling networks. Nature, 1995. 373(6515): p. 573-80.

21. Songyang, Z., et al., SH2 domains recognize specific phosphopeptide sequences. Cell, 1993. 72(5): p. 767-78.
22. Xie, Y., K. Li, and M. C. Hung, Tyrosine phosphorylation of Shc proteins and formation of Shc/Grb2 complex correlate to the transformation of NIH3T3 cells mediated by the point-mutation activated neu. Oncogene, 1995. 10(12): p. 2409-2413.
23. Pelicci, G., et al., A novel transforming protein (SHC) with an SH2 domain is implicated in mitogenic signal transduction. Cell, 1992. 70(1): p. 93-104.
24. Gotoh, N., M. Toyoda, and M. Shibuya, Tyrosine phosphorylation sites at amino acids 239 and 240 of Shc are involved in epidermal growth factor-induced mitogenic signaling that is distinct from Ras/mitogen-activated protein kinase activation. Mol Cell Biol, 1997. 17(4): p. 1824-31.
25. Gotoh, N., A. Tojo, and M. Shibuya, A novel pathway from phosphorylation of tyrosine residues 239/240 of Shc, contributing to suppress apoptosis by IL-3. Embo J, 1996. 15(22): p. 6197-204.
26. Gu, H., et al., New role for Shc in activation of the phosphatidylinositol 3-kinase/Akt pathway. Mol Cell Biol, 2000. 20(19): p. 7109-20.
27. Batzer, A. G., et al., Hierarchy of binding sites for Grb2 and Shc on the epidermal growth factor receptor. Mol Cell Biol, 1994. 14(8): p. 5192-201.
28. Buday, L. and J. Downward, Epidermal growth factor regulates p21ras through the formation of a complex of receptor, Grb2 adaptor protein, and Sos nucleotide exchange factor. Cell, 1993. 73: p. 611-620.
29. Feig, L. A., Guanine-nucleotide exchange factors: a family of positive regulators of Ras and related GTPases. Curr Opin Cell Biol, 1994. 6(2): p. 204-11.
30. Karin, M. and T. Hunter, Transcriptional control by protein phosphorylation: signal transmission from the cell surface to the nucleus. Curr Biol, 1995. 5(7): p. 747-57.
31. Meyer, S., et al., Analysis of the role of the Shc and Grb2 proteins in signal transduction by the v-ErbB protein. Mol Cell Biol, 1994. 14(5): p. 3253-62.
32. Seger, R. and E. G. Krebs, The MAPK signaling cascade. Faseb J, 1995. 9(9): p. 726-35.
33. Segatto, O., et al., Shc products are substrates of erbB-2 kinase. Oncogene, 1993. 8(8): p. 2105-12.
34. Sutherland, R. L., C. K. Watts, and E. A. Musgrove, Cyclin gene expression and growth control in normal and neoplastic human breast epithelium. J Steroid Biochem Mol Biol, 1993. 47(1-6): p. 99-106.
35. Clark, J. W., et al., Effects of tyrosine kinase inhibitors on the proliferation of human breast cancer cell lines and proteins important in the Ras signaling pathway. Int J Cancer, 1996. 65(2): p. 186-91.
36. Janes, P. W., et al., Activation of the Ras signalling pathway in human breast cancer cells overexpressing erbB-2. Oncogene, 1994. 9(12): p. 3601-3608.
37. Sepp-Lorenzino, L., et al., Signal transduction pathways induced by heregulin in MDA-MB-453 breast cancer cells. Oncogene, 1996. 12(8): p. 1679-87.
38. Stevenson, L. A. and A. R. J. Frackelton, Constitutively tyrosine phosphorylated p52 Shc in breast cancer cells: Correlation with ErbB2 and p66 Shc expression. Breast Cancer Research & Treatment, 1998. 49: p. 119-128.
39. Gotoh, N., et al., The SH2 domain of Shc suppresses EGF-induced mitogenesis in a dominant negative manner. Oncogene, 1995. 11(12): p. 2525-2533.
40. Pelicci, G., et al., The motogenic and mitogenic responses to HGF are amplified by the Shc adaptor protein. Oncogene, 1995. 10(8): p. 1631-8.
41. Sasaoka, T., et al., Evidence for a functional role of Shc proteins in mitogenic signaling induced by insulin, insulin-like growth factor-i, and epidermal growth factor. J Biol Chem, 1994. 269(18): p. 13689-94.
42. Stevenson, L. A., K. S. Ravichandran, and A. R. J. Frackelton, Shc dominant negative disrupts cell cycle progression in both G0/G1 and G2/M of ErbB2 positive breast cancer cells. Cell Growth & Differentiation, 1999. 10(1): p. 61-71.
43. Rozakis-Adcock, M., et al., Association of the Shc and Grb2/Sem5 SH2-containing proteins is implicated in activation of the Ras pathway by tyrosine kinases. Nature, 1992. 360(6405): p. 689-92.
44. Migliaccio, E., et al., Opposite effects of the p52shc/p46shc and p66shc splicing isoforms on the EGF receptor-MAP kinase-fos signalling pathway. Embo J, 1997. 16(4): p. 706-16.
45. Dickson, R. B., et al., Breast cancer: influence of endocrine hormones, growth factors and genetic alterations. Adv Exp Med Biol, 1993. 330: p. 119-41.
46. Ennis, B. W., et al., Anti-epidermal growth factor receptor antibodies inhibit the autocrine-stimulated growth of MDA-468 human breast cancer cells. Mol Endocrinol, 1989. 3(11): p. 1830-8.
47. Hines, S. J., et al., Coexpression of the c-kit and stem cell factor genes in breast carcinomas. Cell Growth Differ, 1995. 6(6): p. 769-79.
48. Buday, L., P. H. Warne, and J. Downward, Downregulation of the Ras activation pathway by MAP kinase phosphorylation of Sos. Oncogene, 1995. 11(7): p. 1327-31.
49. Boylan, J. M. and P. A. Gruppuso, Uncoupling of hepatic, epidermal growth factor-mediated mitogen-activated protein kinase activation in the fetal rat. J Biol Chem, 1998. 273(6): p. 3784-90.
50. Zhao, H., et al., Insulin receptor-mediated dissociation of, Grb2 from Sos involves phosphorylation of Sos by kinase(s) other than extracellular signal-regulated kinase. J Biol Chem, 1998. 273(20): p. 12061-7.
51. Dong, C., et al., SOS phosphorylation and disassociation of the Grb2-SOS complex by the ERK and JNK signaling pathways. J Biol Chem, 1996. 271(11): p. 6328-32.
52. Li, L., R. W. Garden, and J. V. Sweedler, Single-cell MALDI: a new tool for direct peptide profiling. Trends Biotechnol, 2000. 18(4): p. 151-60.
53. Whittal, R. M., B. O. Keller, and L. Li, Nanoliter chemistry combined with mass spectrometry for peptide mapping of proteins from single mammalian cell lysates. Anal Chem, 1998. 70(24): p. 5344-7.
54. Clark J W, Santos-Moore A, Stevenson L E, and Frackelton A R Jr. Effects of tyrosine kinase inhibitors on the proliferation of human breast cancer cell lines and proteins important in the Ras signaling pathway. Int. J. Cancer 65:186-191, 1995.
55. Stevenson L E. Ph.D. Thesis. Brown University. 1998.

What is claimed is:

1. A method of determining, for a subject diagnosed as afflicted with a breast tumor, the likelihood of the subject suffering a recurrence of the tumor following primary treatment, which method comprises determining the amount of p66-She and/or phosphorylated Shc present in the cancerous cells of the tumor, and comparing the amount so determined to a standard, wherein the standard comprises the amount of p66-She and/or phosphorylated Shc present in the cancerous cells of a tumor from a subject with no recurrence of the tumor, and wherein low levels of p66-Shc compared to the levels of p66-She in the standard, high levels of phosphorylated Shc compared to the levels of phosphorylated Shc in the standard, and/or low levels of p66-Shc coupled with high levels of phosphorylated Shc compared to the levels of p66-Shc coupled with the levels of phosphorylated Shc in the standard indicates that the subject will suffer a recurrence of the tumor, thereby determining the likelihood of recurrence.

2. A method for determining, for a subject diagnosed as afflicted with a breast tumor, the likelihood of the subject suffering a recurrence of the tumor following primary treatment, which method comprises determining the ratio of p66-Shc to phosphorylated Shc and/or the ratio of phosphorylated Shc to p66-Shc present in the cancerous cells of the tumor, and comparing the ratio(s) so determined to a standard, wherein the standard comprises the amount of p66-Shc and/or phosphorylated Shc present in the cancerous cells of a tumor from a subject with no recurrence of the tumor, and wherein low levels of p66-Shc coupled with high levels of phosphorylated Shc compared to the levels of p66-Shc coupled with the levels of phosphorylated Shc in the standard indicates that the subject will suffer a recurrence of the tumor thereby determining the likelihood of recurrence.

3. A method for determining, for a subject diagnosed as afflicted with a breast tumor, the likelihood of the subject suffering a recurrence of the tumor following primary treatment, which method comprises determining the amounts of p66-Shc and/or phosphorylated Shc in each of a plurality of cancerous cells present in the tumor, and comparing the amounts so determined with a standard, wherein the standard comprises the amount of p66-Shc and/or phosphorylated Shc present in the cancerous cells of a tumor from a subject with no recurrence of the tumor, and wherein low levels of p66-Shc compared to the levels of p66-Shc in the standard, high levels of phosphorylated Shc compared to the levels of phosphorylated Shc in the standard, and/or low levels of p66-Shc coupled with high levels of phosphorylated Shc compared to the levels of p66-Shc coupled with the levels of phosphorylated Shc in the standard indicates that the subject will suffer a recurrence of the tumor thereby determining the likelihood of recurrence.

4. A method for determining, for a subject diagnosed as afflicted with a breast tumor, the likelihood of the subject suffering a recurrence of the tumor following primary treatment, which method comprises determining the ratios of p66-Shc to phosphorylated Shc and/or the ratios of phosphorylated Shc to p66-Shc in each of a plurality of cancerous cells present in the tumor, and comparing the ratios so determined with a standard, wherein the standard comprises the amount of p66-She and/or phosphorylated Shc present in the cancerous cells of a tumor from a subject with no recurrence of the tumor, and wherein low levels of p66-She coupled with high levels of phosphorylated Shc compared to the levels of p66-Shc coupled with the levels of phosphorylated Shc in the standard indicates that the subject will suffer a recurrence of the tumor thereby determining the likelihood of recurrence.

5. The method of claim 3 wherein the subject is human.

6. The method of claim 3 wherein the subject's lymph nodes are free of tumor cells.

7. The method of claim 3 wherein a detectable antibody that specifically binds to p66-Shc, a detectable antibody that specifically binds to phosphorylated Shc, flow cytometry, immunohistochemistry or a combination thereof is used to determine the amounts of p66-Shc or phosphorylated Shc.

8. The method of claim 3 wherein the tumor cell is present in a tissue sample.

9. The method of claim 3 wherein the primary treatment comprises a treatment selected from the group consisting of surgery, radiation, hormone therapy and chemotherapy.

10. The method of claim 1, wherein only the amount of p66-Shc is determined.

11. The method of claim 1, wherein only the amount of phosphorylated Shc is determined.

12. The method of claim 1, wherein the amounts of both p66-Shc and phosphorylated Shc are determined.

13. The method of claim 1 wherein the subject is human.

14. The method of claim 2 wherein the subject is human.

15. The method of claim 4 wherein the subject is human.

16. The method of claim 1 wherein the subject's lymph nodes are free of tumor cells.

17. The method of claim 2 wherein the subject's lymph nodes are free of tumor cells.

18. The method of claim 4 wherein the subject's lymph nodes are free of tumor cells.

19. The method of claim 1 wherein a detectable antibody that specifically binds to p66-Shc, a detectable antibody that specifically binds to phosphorylated Shc, flow cytometry, immunohistochemistry or a combination thereof is used to determine the amounts of p66-Shc and phosphorylated Shc.

20. The method of claim 2 wherein a detectable antibody that specifically binds to p66-Shc, a detectable antibody that specifically binds to phosphorylated Shc, flow cytometry, immunohistochemistry or a combination thereof is used to determine the amounts of p66-She and phosphorylated Shc.

21. The method of claim 4 wherein the determination step is selected from the group consisting of: the use of a detectable antibody that specifically binds to p66-Shc, the use of a detectable antibody that specifically binds phosphorylated Shc, the use of flow cytometry, the use of immunohistochemistry and a combination thereof.

22. The method of claim 1 wherein the tumor cell is present in a tissue sample.

23. The method of claim 2 wherein the tumor cell is present in a tissue sample.

24. The method of claim 4 wherein the tumor cell is present in a tissue sample.

25. The method of claim 1 wherein the primary treatment comprises a treatment selected from the group consisting of surgery, radiation, hormone therapy and chemotherapy.

26. The method of claim 2 wherein the primary treatment comprises a treatment selected from the group consisting of surgery, radiation, hormone therapy and chemotherapy.

27. The method of claim 4 wherein the primary treatment comprises a treatment selected from the group consisting of surgery, radiation, hormone therapy and chemotherapy.

* * * * *

UNITED STATES PATENT AND TRADEMARK OFFICE
CERTIFICATE OF CORRECTION

| | | |
|---|---|---|
| PATENT NO. | : 7,910,314 B2 | |
| APPLICATION NO. | : 10/376538 | |
| DATED | : March 22, 2011 | |
| INVENTOR(S) | : A. Raymond Frackelton, Jr. and Pamela A. Davol | |

It is certified that error appears in the above-identified patent and that said Letters Patent is hereby corrected as shown below:

On the face of the patent in the References Cited Field (56) under Other Publications please insert the following references:

--Davol, P.A., *et al.*, Shc Proteins Are Strong Independent Prognostic Markers for Both Node-Negative and Node-Positive Primary Breast Cancer," *Cancer Research*, 63: 6772-6783, (2003).--

--Lotti, L.V., *et al.*, "Shc Proteins Are Localized on Endoplasmic Reticulum Membranes and Are Redistributed After Tyrosine Kinase Receptor Activation," *Molecular and Cellular Biology*, 16(5): 1946-1954, (1996).--

--Ouyang, X., *et al.*, "Multisite Phosphotyping of the ErbB-2 Oncoprotein in Human Breast Cancer," *Molecular Diagnosis*, 6(1): 17-25, (2001).

In Claim 1, Column 27, Lines 38, 41 and 44 delete "She" and insert --Shc--

In Claim 4, Column 28, Lines 54, 57 and 59 delete "She" and insert --Shc--

Signed and Sealed this
Tenth Day of May, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: peptide used to raise antibody to PY-sch
<220> FEATURE:
<223> OTHER INFORMATION: Position 7 (Tyr) = phosphorylated

<400> SEQUENCE: 1

Leu Phe Asp Asp Pro Ser Tyr Val Asn Val Gln Asn Leu Cys
 1               5                  10

<210> SEQ ID NO 2
<211> LENGTH: 17
<212> TYPE: PRT
<213> ORGANISM: Artificial Sequence
<220> FEATURE:
<223> OTHER INFORMATION: hydrophilic peptide derived from p66 sch1-110
      CH2 domain

<400> SEQUENCE: 2

Ser Gly Ser Thr Pro Pro Glu Glu Leu Pro Ser Pro Ser Ala Ser Ser
 1               5                  10                  15

Leu